(12) United States Patent
Tordella et al.

(10) Patent No.: US 7,871,387 B2
(45) Date of Patent: Jan. 18, 2011

(54) COMPRESSION SLEEVE CONVERTIBLE IN LENGTH

(75) Inventors: Elise Tordella, Norfolk, MA (US); Christopher Tesluk, Providence, RI (US); Malcolm Bock, Medfield, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 936 days.

(21) Appl. No.: 10/784,607

(22) Filed: Feb. 23, 2004

(65) Prior Publication Data

US 2005/0187503 A1    Aug. 25, 2005

(51) Int. Cl.
A61H 23/04    (2006.01)

(52) U.S. Cl. .................. 601/151; 601/152; 128/DIG. 20

(58) Field of Classification Search ......... 601/148–152; 602/13, 78; 128/DIG. 20; 2/70, 269; 137/614, 137/614.02, 614.03; 251/149.1; 285/124.1
See application file for complete search history.

(56) References Cited

U.S. PATENT DOCUMENTS

| 910,689 | A | 1/1909 | Kelly et al. |
|---|---|---|---|
| 1,510,482 | A | 10/1924 | Kramer |
| 1,608,239 | A | 11/1926 | Rosett |
| 1,670,318 | A | 5/1928 | Shaff |
| 1,695,848 | A | 12/1928 | Higgins |
| 1,883,240 | A | 10/1932 | Phelan |
| 2,199,408 | A | 5/1940 | Liberte |
| 2,280,485 | A | 4/1942 | Harris |
| 2,533,504 | A | 12/1950 | Poor |
| 2,628,850 | A | 2/1953 | Summerville |
| 2,638,915 | A * | 5/1953 | Mitchell ................ 137/599.02 |
| 2,676,587 | A | 4/1954 | Corcoran |
| 2,694,393 | A | 11/1954 | Simpson |
| 2,694,395 | A | 11/1954 | Brown ........................ 128/38 |
| 2,880,721 | A | 4/1959 | Corcoran |
| 2,896,612 | A | 7/1959 | Bates et al. |
| 2,998,817 | A | 9/1961 | Armstrong |
| 3,057,001 | A | 10/1962 | Rapata |
| 3,164,152 | A | 1/1965 | Nicoll ........................ 128/87 |

(Continued)

FOREIGN PATENT DOCUMENTS

DE    19846922 A1    4/2000

(Continued)

OTHER PUBLICATIONS

Tyco Healthcare Kendall, SCD Response Catalog, Mar. 2000, pp. 1-2.

(Continued)

*Primary Examiner*—Danton DeMille

(57) ABSTRACT

A compression apparatus is provided that includes a sleeve configured for disposal about a limb. The sleeve includes a first portion defining a first expandable chamber and a second portion defining a second expandable chamber and a third expandable chamber. The second portion includes a connector in fluid communication with a pressurized fluid source and the chambers thereby facilitating fluid communication between the pressurized fluid source and the chambers. The first portion is removable from the second portion. The first portion may be connected to the second portion via a perforated attachment. The sleeve may define at least one ventilation opening. The connector can communicate with the chambers via a tubular pathway. The sleeve may be convertible from a length extending from below a knee to above the knee, to a length extending solely below the knee.

26 Claims, 8 Drawing Sheets

U.S. PATENT DOCUMENTS

| | | | |
|---|---|---|---|
| 3,245,405 A | 4/1966 | Gardner | |
| 3,287,031 A | 11/1966 | Simmons et al. | |
| 3,288,132 A * | 11/1966 | Meredith | 601/152 |
| 3,351,055 A | 11/1967 | Gottfried | |
| 3,454,010 A | 7/1969 | Lilligren et al. | 128/327 |
| 3,469,769 A | 9/1969 | Guenther | |
| 3,469,863 A | 9/1969 | Riester et al. | |
| 3,561,435 A | 2/1971 | Nicholson | 128/82.1 |
| 3,568,227 A | 3/1971 | Dunham | |
| 3,606,880 A | 9/1971 | Ogle, Jr. | |
| 3,701,173 A | 10/1972 | Whitney | |
| 3,728,875 A | 4/1973 | Hartigan et al. | 66/172 E |
| 3,733,577 A | 5/1973 | Hammond | |
| 3,760,795 A | 9/1973 | Adelhed | |
| 3,771,519 A | 11/1973 | Haake | |
| 3,786,805 A | 1/1974 | Tourin | 128/87 R |
| 3,824,992 A | 7/1974 | Nicholson et al. | |
| 3,826,249 A | 7/1974 | Lee et al. | 128/24 R |
| 3,862,629 A * | 1/1975 | Rotta | 601/150 |
| 3,868,952 A | 3/1975 | Hatton | |
| 3,877,426 A | 4/1975 | Nirschl | 128/165 |
| 3,899,210 A | 8/1975 | Samhammer et al. | |
| 3,901,221 A | 8/1975 | Nicholson et al. | 128/24 R |
| 3,906,937 A | 9/1975 | Aronson | |
| 3,920,006 A | 11/1975 | Lapidus | 128/24.1 |
| D239,981 S | 5/1976 | Arluck et al. | |
| 3,955,565 A | 5/1976 | Johnson, Jr. | |
| 4,013,069 A | 3/1977 | Hasty | 128/24 R |
| 4,029,087 A | 6/1977 | Dye et al. | 128/24 R |
| 4,030,488 A | 6/1977 | Hasty | 128/24 R |
| 4,054,129 A | 10/1977 | Byars et al. | |
| 4,066,084 A | 1/1978 | Tillander | 128/327 |
| 4,076,022 A | 2/1978 | Walker | |
| 4,091,804 A | 5/1978 | Hasty | 128/24 R |
| 4,146,021 A | 3/1979 | Brosseau et al. | |
| 4,149,529 A | 4/1979 | Copeland et al. | |
| 4,153,050 A | 5/1979 | Bishop et al. | |
| 4,156,425 A | 5/1979 | Arkans | 128/24 R |
| 4,198,961 A | 4/1980 | Arkans | 128/24 R |
| 4,202,312 A | 5/1980 | Mori et al. | 123/210 |
| 4,202,325 A | 5/1980 | Villari et al. | 128/24 R |
| 4,206,751 A | 6/1980 | Schneider | 601/152 |
| 4,207,875 A | 6/1980 | Arkans | 128/24 R |
| 4,207,876 A | 6/1980 | Annis | 128/24 R |
| 4,219,892 A | 9/1980 | Rigdon | |
| 4,253,449 A | 3/1981 | Arkans et al. | 128/24 R |
| 4,267,611 A | 5/1981 | Agulnick | |
| 4,270,527 A | 6/1981 | Peters et al. | |
| 4,280,485 A * | 7/1981 | Arkans | 601/152 |
| 4,294,240 A | 10/1981 | Thill | |
| 4,300,245 A | 11/1981 | Saunders | |
| 4,308,862 A | 1/1982 | Kalmar | |
| 4,311,135 A | 1/1982 | Brueckner et al. | |
| 4,320,746 A | 3/1982 | Arkans et al. | 601/152 |
| 4,351,872 A | 9/1982 | Brosseau et al. | |
| 4,355,632 A | 10/1982 | Sandman | 128/24 R |
| 4,372,297 A | 2/1983 | Perlin | |
| 4,375,217 A | 3/1983 | Arkans | 128/24 |
| 4,379,217 A | 4/1983 | Youmans | |
| 4,402,312 A | 9/1983 | Villari et al. | |
| 4,408,599 A | 10/1983 | Mummert | 128/24 R |
| 4,417,587 A | 11/1983 | Ichinomiya et al. | |
| 4,442,834 A | 4/1984 | Tucker et al. | 128/90 |
| 4,453,538 A | 6/1984 | Whitney | 128/24 R |
| 4,522,197 A * | 6/1985 | Hasegawa | 601/40 |
| 4,531,516 A * | 7/1985 | Poole et al. | 602/13 |
| 4,547,919 A | 10/1985 | Wang | |
| 4,580,816 A | 4/1986 | Campbell et al. | 285/321 |
| 4,597,384 A | 7/1986 | Whitney | 601/152 |
| 4,614,179 A | 9/1986 | Gardner et al. | 128/64 |
| 4,614,180 A | 9/1986 | Gardner et al. | 128/64 |
| 4,624,244 A | 11/1986 | Taheri | |
| 4,624,248 A * | 11/1986 | Poole et al. | 602/13 |
| 4,650,452 A | 3/1987 | Jensen | |
| 4,657,003 A | 4/1987 | Wirtz | |
| 4,682,588 A | 7/1987 | Curlee | |
| 4,696,289 A | 9/1987 | Gardner et al. | 128/64 |
| 4,699,424 A | 10/1987 | Andres et al. | |
| 4,702,232 A | 10/1987 | Gardner et al. | 128/64 |
| 4,703,750 A | 11/1987 | Sebastian et al. | |
| 4,706,658 A | 11/1987 | Cronin | |
| 4,721,101 A | 1/1988 | Gardner et al. | 128/64 |
| 4,722,332 A | 2/1988 | Saggers | 602/62 |
| 4,730,606 A | 3/1988 | Leininger | 128/75 |
| 4,754,993 A | 7/1988 | Kraynick | |
| 4,762,121 A | 8/1988 | Shienfeld | 128/64 |
| 4,762,504 A | 8/1988 | Michaels et al. | |
| 4,773,397 A | 9/1988 | Wright et al. | |
| 4,804,208 A | 2/1989 | Dye | |
| 4,805,620 A | 2/1989 | Meistrell | |
| 4,809,684 A | 3/1989 | Gardner et al. | |
| 4,827,912 A | 5/1989 | Carrington et al. | 601/152 |
| 4,832,010 A | 5/1989 | Lerman | |
| RE32,939 E | 6/1989 | Gardner et al. | 601/152 |
| RE32,940 E | 6/1989 | Gardner et al. | 601/152 |
| 4,836,194 A | 6/1989 | Sebastian et al. | |
| 4,836,691 A | 6/1989 | Suzuki et al. | |
| 4,841,956 A | 6/1989 | Gardner et al. | 128/64 |
| D302,301 S | 7/1989 | Robinette-Lehman | D24/143 |
| 4,846,160 A | 7/1989 | Gardner et al. | |
| 4,846,189 A | 7/1989 | Sun | |
| 4,867,699 A | 9/1989 | Oda et al. | |
| 4,869,265 A | 9/1989 | McEwen | |
| 4,872,736 A | 10/1989 | Myers et al. | |
| 4,876,788 A | 10/1989 | Steer et al. | |
| 4,883,073 A | 11/1989 | Aziz | 128/878 |
| 4,886,053 A | 12/1989 | Neal | |
| 4,898,160 A | 2/1990 | Brownlee | |
| 4,938,208 A | 7/1990 | Dye | 128/87 R |
| 4,938,226 A | 7/1990 | Danielsson et al. | |
| 4,945,571 A | 8/1990 | Calvert | |
| 4,947,834 A | 8/1990 | Kartheus et al. | |
| 4,960,115 A | 10/1990 | Ranciato | |
| 4,979,953 A | 12/1990 | Spence | |
| 5,007,411 A | 4/1991 | Dye | 601/151 |
| 5,014,681 A | 5/1991 | Neeman et al. | 128/64 |
| 5,022,387 A | 6/1991 | Hasty | 601/152 |
| 5,031,604 A | 7/1991 | Dye | 601/152 |
| 5,041,025 A | 8/1991 | Haitmanek | |
| 5,048,536 A | 9/1991 | McEwen | |
| 5,052,377 A | 10/1991 | Frajdenrajch | |
| 5,062,414 A | 11/1991 | Grim | 128/68.1 |
| 5,069,219 A | 12/1991 | Knoblich | |
| 5,109,832 A | 5/1992 | Proctor et al. | |
| 5,117,812 A | 6/1992 | McWhorter | |
| 5,139,475 A | 8/1992 | Robicsek | |
| 5,139,476 A | 8/1992 | Peters | |
| 5,146,932 A | 9/1992 | McCabe | |
| 5,156,629 A | 10/1992 | Shane et al. | |
| 5,168,576 A | 12/1992 | Krent et al. | |
| D332,495 S | 1/1993 | Lake | |
| 5,176,406 A | 1/1993 | Straghan | |
| 5,179,941 A | 1/1993 | Siemssen et al. | |
| 5,181,522 A | 1/1993 | McEwen | |
| 5,186,163 A | 2/1993 | Dye | 601/27 |
| 5,193,549 A | 3/1993 | Bellin et al. | |
| 5,211,162 A | 5/1993 | Gillen, Jr. et al. | |
| 5,217,384 A | 6/1993 | Merten et al. | |
| 5,219,185 A | 6/1993 | Oddenino | |
| 5,226,245 A | 7/1993 | Lamont | |
| 5,226,564 A | 7/1993 | Steer et al. | |
| 5,230,335 A | 7/1993 | Johnson, Jr. et al. | 128/400 |
| 5,245,990 A | 9/1993 | Bertinin | |
| 5,249,830 A | 10/1993 | Calmettes et al. | |

| | | | | | | |
|---|---|---|---|---|---|---|
| 5,259,397 A | 11/1993 | McCabe | | 5,725,485 A | 3/1998 | Ribando et al. |
| 5,263,473 A | 11/1993 | McWhorter ................. 601/27 | | 5,728,057 A | 3/1998 | Ouellette et al. |
| 5,273,254 A | 12/1993 | McNaughton et al. | | 5,730,710 A | 3/1998 | Eichhorn et al. |
| 5,277,695 A | 1/1994 | Johnson, Jr. et al. .......... 602/14 | | 5,741,295 A | 4/1998 | McEwen |
| 5,277,697 A | 1/1994 | France et al. | | 5,743,755 A | 4/1998 | Aoki |
| 5,314,455 A | 5/1994 | Johnson, Jr. et al. ........ 607/104 | | 5,746,213 A | 5/1998 | Marks |
| 5,330,366 A | 7/1994 | Tsuji et al. | | 5,769,800 A | 6/1998 | Gelfand et al. |
| 5,334,135 A | 8/1994 | Grim et al. | | 5,769,801 A | 6/1998 | Tumey et al. |
| 5,342,285 A * | 8/1994 | Dye ........................... 601/151 | | 5,772,880 A | 6/1998 | Lynn et al. |
| 5,354,260 A | 10/1994 | Cook ......................... 602/13 | | 5,790,998 A | 8/1998 | Crescimbeni |
| 5,370,423 A | 12/1994 | Guest | | 5,795,312 A * | 8/1998 | Dye ........................... 601/151 |
| 5,378,224 A | 1/1995 | Billotti | | 5,797,851 A | 8/1998 | Byrd |
| 5,383,894 A | 1/1995 | Dye ........................... 606/201 | | 5,823,981 A | 10/1998 | Grim et al. |
| 5,383,919 A | 1/1995 | Kelly et al. | | 5,830,164 A | 11/1998 | Cone et al. |
| 5,385,538 A | 1/1995 | Mann | | 5,833,639 A | 11/1998 | Nunes et al. |
| 5,387,110 A | 2/1995 | Kantner et al. | | 5,840,049 A | 11/1998 | Tumey et al. ................ 601/149 |
| 5,389,065 A | 2/1995 | Johnson, Jr. .................. 602/27 | | 5,843,007 A | 12/1998 | McEwen et al. ............. 601/152 |
| 5,391,141 A | 2/1995 | Hamilton | | D403,775 S | 1/1999 | Davis et al. |
| 5,399,153 A | 3/1995 | Caprio, Jr. et al. | | D405,884 S | 2/1999 | Roper |
| D357,736 S | 4/1995 | Dye | | 5,876,359 A | 3/1999 | Bock et al. .................. 601/150 |
| 5,403,265 A | 4/1995 | Berguer et al. | | 5,881,769 A | 3/1999 | Hopson |
| 5,407,421 A | 4/1995 | Goldsmith | | 5,891,065 A | 4/1999 | Cariapa et al. |
| D358,216 S | 5/1995 | Dye ........................... D24/206 | | 5,897,142 A | 4/1999 | Kulevsky |
| 5,413,142 A | 5/1995 | Johnson et al. .......... 137/515.5 | | D411,301 S | 6/1999 | Hampson et al. ............. D24/189 |
| 5,413,582 A | 5/1995 | Eaton | | 5,925,010 A | 7/1999 | Caprio, Jr. |
| 5,419,757 A | 5/1995 | Daneshvar | | 5,931,797 A | 8/1999 | Tumey et al. ................ 601/152 |
| 5,435,009 A | 7/1995 | Schild et al. ..................... 2/22 | | 5,938,628 A * | 8/1999 | Oguri et al. .................. 601/150 |
| 5,437,595 A | 8/1995 | Smith | | 5,951,502 A | 9/1999 | Peeler et al. ................. 601/149 |
| 5,437,610 A | 8/1995 | Cariapa et al. ............... 601/152 | | 5,957,872 A | 9/1999 | Flick |
| 5,441,533 A | 8/1995 | Johnson et al. .............. 607/104 | | 5,966,763 A | 10/1999 | Thomas et al. |
| 5,443,289 A | 8/1995 | Guest | | 5,968,072 A | 10/1999 | Hite et al. |
| 5,443,440 A | 8/1995 | Tumey et al. | | 5,976,099 A | 11/1999 | Kellogg |
| 5,449,341 A | 9/1995 | Harris | | 5,976,300 A | 11/1999 | Buchanan et al. |
| 5,450,858 A | 9/1995 | Zablotsky et al. | | 5,988,704 A | 11/1999 | Ryhman ...................... 285/307 |
| 5,451,201 A | 9/1995 | Prengler | | 5,989,204 A | 11/1999 | Lina ............................ 601/152 |
| 5,453,081 A | 9/1995 | Hansen | | 5,991,654 A | 11/1999 | Tumey et al. ................ 600/479 |
| 5,462,517 A | 10/1995 | Mann | | 5,997,495 A | 12/1999 | Cook et al. ................... 602/62 |
| D363,988 S | 11/1995 | Dye | | 6,001,119 A | 12/1999 | Hampson et al. ............. 606/202 |
| 5,466,250 A | 11/1995 | Johnson, Jr. et al. ........ 607/104 | | 6,007,559 A | 12/1999 | Arkans ........................ 606/201 |
| 5,470,156 A | 11/1995 | May | | 6,010,471 A | 1/2000 | Ben-Noon |
| 5,478,119 A | 12/1995 | Dye ........................... 285/26 | | 6,036,718 A | 3/2000 | Ledford et al. |
| 5,489,252 A | 2/1996 | May ........................ 383/210.1 | | 6,048,326 A | 4/2000 | Davis et al. |
| 5,489,259 A | 2/1996 | Jacobs et al. ................... 602/13 | | 6,051,016 A | 4/2000 | Mesaros et al. |
| 5,496,262 A | 3/1996 | Johnson, Jr. et al. ........ 601/152 | | 6,062,244 A | 5/2000 | Arkans ........................... 137/1 |
| 5,511,552 A | 4/1996 | Johnson | | 6,066,217 A | 5/2000 | Dibble et al. |
| 5,513,658 A | 5/1996 | Goseki | | 6,080,120 A | 6/2000 | Sandman et al. |
| 5,514,081 A | 5/1996 | Mann ........................... 602/20 | | D428,153 S | 7/2000 | Davis |
| 5,518,416 A | 5/1996 | Kantner et al. | | 6,105,933 A | 8/2000 | Kanno et al. |
| 5,527,267 A | 6/1996 | Billotti | | 6,110,135 A | 8/2000 | Madow et al. |
| 5,554,105 A | 9/1996 | Taylor | | 6,126,683 A | 10/2000 | Momtaheni |
| D376,013 S | 11/1996 | Sandman et al. ............ D24/169 | | 6,129,688 A | 10/2000 | Arkans ........................ 601/152 |
| 5,575,762 A | 11/1996 | Peeler et al. ................. 601/152 | | 6,135,116 A | 10/2000 | Vogel et al. .................. 128/898 |
| 5,578,055 A | 11/1996 | McEwen | | 6,145,143 A | 11/2000 | Hicks et al. |
| 5,584,798 A | 12/1996 | Fox ........................... 601/152 | | 6,149,600 A | 11/2000 | Poorman-Ketchum |
| 5,588,954 A | 12/1996 | Ribando et al. | | 6,152,495 A | 11/2000 | Hoffmann et al. ....... 285/148.19 |
| 5,588,955 A | 12/1996 | Johnson, Jr. et al. ........ 601/152 | | 6,152,893 A | 11/2000 | Pigg et al. ..................... 602/75 |
| 5,588,956 A | 12/1996 | Billotti | | 6,171,271 B1 | 1/2001 | Hörnberg |
| 5,591,200 A | 1/1997 | Cone et al. ................... 606/201 | | 6,179,796 B1 | 1/2001 | Waldridge |
| 5,591,337 A | 1/1997 | Lynn et al. | | 6,197,045 B1 | 3/2001 | Carson |
| 5,603,690 A | 2/1997 | Barry | | 6,203,510 B1 | 3/2001 | Takeuchi et al. |
| 5,609,570 A | 3/1997 | Lamont | | 6,209,159 B1 | 4/2001 | Murphy |
| 5,626,556 A | 5/1997 | Tobler et al. ................. 601/151 | | 6,212,719 B1 | 4/2001 | Thomas et al. |
| 5,626,557 A | 5/1997 | Mann | | 6,231,507 B1 | 5/2001 | Zikorus et al. |
| 5,634,889 A | 6/1997 | Gardner et al. .............. 601/151 | | 6,231,532 B1 | 5/2001 | Watson et al. ............... 601/150 |
| 5,649,954 A | 7/1997 | McEwen | | 6,238,230 B1 | 5/2001 | Sadler et al. |
| 5,653,244 A | 8/1997 | Shaw ........................ 128/882 | | 6,245,023 B1 | 6/2001 | Clemmons |
| D383,547 S | 9/1997 | Mason et al. | | 6,254,554 B1 | 7/2001 | Turtzo |
| 5,664,270 A | 9/1997 | Bell et al. | | 6,257,626 B1 | 7/2001 | Campau ....................... 285/81 |
| 5,669,872 A | 9/1997 | Fox ........................... 601/152 | | 6,257,627 B1 | 7/2001 | Fujiwara et al. ............. 285/305 |
| 5,674,262 A | 10/1997 | Tumey ........................ 607/48 | | 6,273,866 B2 | 8/2001 | Thomas et al. |
| 5,678,558 A | 10/1997 | Johnson | | 6,290,662 B1 | 9/2001 | Morris et al. ................ 601/149 |
| 5,695,453 A | 12/1997 | Neal | | 6,296,617 B1 | 10/2001 | Peeler et al. ................. 601/152 |
| 5,711,757 A | 1/1998 | Bryant ........................ 601/23 | | 6,315,745 B1 | 11/2001 | Kloecker ..................... 602/13 |

| | | |
|---|---|---|
| 6,319,215 B1 | 11/2001 | Manor et al. ............... 601/152 |
| 6,322,530 B1 | 11/2001 | Johnson, Jr. et al. .......... 602/65 |
| 6,336,935 B1 | 1/2002 | Davis et al. |
| 6,338,723 B1 | 1/2002 | Carpenter et al. |
| 6,349,506 B1 | 2/2002 | Pace et al. |
| 6,358,219 B1 | 3/2002 | Arkans ..................... 601/152 |
| 6,361,496 B1 | 3/2002 | Zikorus et al. |
| 6,368,357 B1 | 4/2002 | Schon et al. ................. 623/37 |
| 6,385,864 B1 | 5/2002 | Sell, Jr. et al. |
| 6,387,065 B1 | 5/2002 | Tumey ..................... 601/152 |
| 6,394,131 B1 | 5/2002 | Fross et al. |
| 6,402,879 B1 | 6/2002 | Tawney et al. |
| 6,421,859 B1 | 7/2002 | Hicks et al. .................. 5/722 |
| 6,423,053 B1 | 7/2002 | Lee ......................... 604/533 |
| 6,436,064 B1 | 8/2002 | Kloecker ................... 602/13 |
| 6,440,093 B1 | 8/2002 | McEwen et al. ........... 601/150 |
| 6,447,460 B1 | 9/2002 | Zheng et al. ............... 600/549 |
| 6,447,467 B1 | 9/2002 | Barak ...................... 601/149 |
| 6,463,934 B1 | 10/2002 | Johnson, Jr. et al. ......... 128/898 |
| 6,468,237 B1 | 10/2002 | Lina ........................ 601/150 |
| 6,478,757 B1 | 11/2002 | Barak ...................... 601/151 |
| 6,488,643 B1 | 12/2002 | Tumey et al. ............... 602/13 |
| 6,493,568 B1 | 12/2002 | Bell et al. ................... 600/323 |
| 6,494,852 B1 | 12/2002 | Barak et al. ................ 601/151 |
| 6,508,205 B1 | 1/2003 | Zink |
| 6,520,926 B2 | 2/2003 | Hall |
| 6,527,727 B2 | 3/2003 | Itonaga et al. |
| 6,537,099 B2 | 3/2003 | Herlinger et al. |
| 6,537,298 B2 | 3/2003 | Dedo |
| 6,540,707 B1 | 4/2003 | Stark et al. |
| 6,544,202 B2 | 4/2003 | McEwen et al. ........... 601/150 |
| 6,547,284 B2 | 4/2003 | Rose et al. |
| 6,549,748 B2 | 4/2003 | Miura |
| 6,551,280 B1 | 4/2003 | Knighton et al. |
| 6,554,785 B1 | 4/2003 | Sroufe et al. |
| 6,557,704 B1 | 5/2003 | Randolph ................... 206/363 |
| 6,558,338 B1 | 5/2003 | Wasserman |
| 6,589,267 B1 | 7/2003 | Hui |
| 6,589,534 B1 | 7/2003 | Shaul et al. ............... 424/227.1 |
| 6,592,534 B1 | 7/2003 | Rutt et al. .................. 601/151 |
| D478,995 S | 8/2003 | Cipra et al. |
| 6,616,622 B1 | 9/2003 | Barberio |
| 6,629,941 B1 | 10/2003 | Ishibashi et al. ............ 601/152 |
| 6,645,165 B2 | 11/2003 | Waldridge et al. |
| D484,986 S | 1/2004 | Cipra et al. |
| 6,676,614 B1 | 1/2004 | Hansen et al. |
| 6,719,711 B1 | 4/2004 | Islava |
| 6,726,641 B2 | 4/2004 | Chiang et al. |
| 6,757,516 B2 | 6/2004 | Miura |
| 6,846,294 B2 | 1/2005 | Rastegar et al. |
| 6,846,295 B1 | 1/2005 | Ben-Nun |
| 6,849,057 B2 | 2/2005 | Satou et al. |
| 6,852,089 B2 | 2/2005 | Kloecker et al. |
| 6,860,862 B2 | 3/2005 | Waldridge et al. |
| 6,862,989 B2 | 3/2005 | Belanger et al. |
| 6,866,636 B2 | 3/2005 | Inoue et al. |
| 6,869,409 B2 | 3/2005 | Rothman et al. |
| 6,890,204 B2 | 5/2005 | Yamawaki |
| D506,553 S | 6/2005 | Tesluk |
| 6,945,944 B2 | 9/2005 | Kuiper et al. |
| D510,626 S | 10/2005 | Krahner et al. |
| 6,966,884 B2 | 11/2005 | Waldridge et al. |
| 6,984,215 B2 * | 1/2006 | Shah et al. .................. 601/152 |
| 6,991,613 B2 | 1/2006 | Sensabaugh |
| 7,011,640 B2 | 3/2006 | Patterson et al. |
| 7,022,096 B1 | 4/2006 | Alfieri |
| 7,041,074 B1 | 5/2006 | Averianov et al. |
| 7,044,924 B1 | 5/2006 | Roth et al. |
| 7,048,703 B2 | 5/2006 | Riach |
| D533,668 S | 12/2006 | Brown |
| 7,166,077 B2 | 1/2007 | Millay et al. |
| 7,214,202 B1 | 5/2007 | Vogel et al. |
| 7,217,249 B2 | 5/2007 | Scott |
| D545,972 S | 7/2007 | Wierenga et al. |
| 7,244,483 B2 | 7/2007 | Tawney et al. |
| 7,258,676 B2 | 8/2007 | Calderon et al. |
| D550,367 S | 9/2007 | Nash |
| 7,276,039 B2 | 10/2007 | Garelick et al. |
| 7,278,980 B1 | 10/2007 | Garelick et al. |
| 7,282,038 B2 | 10/2007 | Gillis et al. |
| 7,288,076 B2 | 10/2007 | Grim et al. |
| 7,297,128 B2 | 11/2007 | Binder et al. |
| 7,303,539 B2 | 12/2007 | Binder et al. |
| 7,306,568 B2 | 12/2007 | Diana |
| 7,318,812 B2 | 1/2008 | Taylor et al. |
| D562,461 S | 2/2008 | Nash |
| D562,462 S | 2/2008 | Muir et al. |
| 7,329,232 B2 | 2/2008 | Lipshaw et al. |
| 7,351,217 B2 | 4/2008 | Scherpenborg |
| 7,354,411 B2 | 4/2008 | Perry et al. |
| 7,374,550 B2 | 5/2008 | Hansen et al. |
| D577,124 S | 9/2008 | Freeland et al. |
| 7,465,283 B2 | 12/2008 | Grim et al. |
| 7,468,048 B2 | 12/2008 | Meehan |
| 7,473,816 B2 | 1/2009 | Hall |
| D594,561 S | 6/2009 | Freeland et al. |
| 7,559,908 B2 | 7/2009 | Ravikumar |
| 7,578,799 B2 | 8/2009 | Thorsteinsson et al. |
| 7,591,796 B1 | 9/2009 | Barak et al. |
| 7,591,797 B2 | 9/2009 | Hakonson et al. |
| 7,597,675 B2 | 10/2009 | Ingimundarson et al. |
| 7,618,389 B2 | 11/2009 | Nordt, III et al. |
| 7,625,348 B2 | 12/2009 | Young et al. |
| 7,637,879 B2 | 12/2009 | Barak et al. |
| D608,006 S | 1/2010 | Avitable et al. |
| 7,654,117 B2 | 2/2010 | Barnett |
| 2001/0018564 A1 | 8/2001 | Manor et al. |
| 2002/0042583 A1 | 4/2002 | Barak et al. |
| 2002/0068886 A1 | 6/2002 | Lin |
| 2002/0069731 A1 | 6/2002 | Soucy |
| 2002/0096883 A1 | 7/2002 | Youssefifar |
| 2002/0115949 A1 | 8/2002 | Kuslich et al. |
| 2002/0133106 A1 | 9/2002 | Peled |
| 2003/0036771 A1 | 2/2003 | McEwen et al. |
| 2003/0075923 A1 | 4/2003 | Lepoutre |
| 2003/0083605 A1 | 5/2003 | Edmund |
| 2003/0139696 A1 | 7/2003 | Boukanov et al. ............. 602/41 |
| 2003/0139766 A1 | 7/2003 | McEwen et al. |
| 2003/0199922 A1 | 10/2003 | Buckman |
| 2004/0010212 A1 | 1/2004 | Kuiper et al. |
| 2004/0039317 A1 | 2/2004 | Souney et al. |
| 2004/0054306 A1 | 3/2004 | Roth et al. |
| 2004/0068290 A1 | 4/2004 | Bates et al. |
| 2004/0097860 A1 | 5/2004 | Tauber |
| 2004/0158283 A1 | 8/2004 | Shook et al. |
| 2004/0158285 A1 | 8/2004 | Pillai |
| 2004/0181156 A1 | 9/2004 | Kingsford et al. |
| 2004/0181254 A1 | 9/2004 | Choi et al. |
| 2004/0199090 A1 | 10/2004 | Sanders et al. |
| 2004/0236258 A1 | 11/2004 | Burns et al. |
| 2005/0070828 A1 | 3/2005 | Hampson et al. |
| 2005/0131321 A1 | 6/2005 | Ravikumar |
| 2005/0143683 A1 | 6/2005 | Waldridge et al. |
| 2005/0154336 A1 | 7/2005 | Kloecker et al. |
| 2005/0165333 A1 | 7/2005 | Rothman et al. |
| 2005/0187500 A1 | 8/2005 | Perry et al. |
| 2005/0187501 A1 | 8/2005 | Ravikumar |
| 2005/0187503 A1 | 8/2005 | Tordella et al. |
| 2005/0209545 A1 | 9/2005 | Farrow et al. |
| 2005/0261617 A1 | 11/2005 | Hall |
| 2006/0010574 A1 | 1/2006 | Linnane et al. |
| 2006/0020236 A1 | 1/2006 | Ben-Nun |
| 2006/0135894 A1 | 6/2006 | Linnane et al. |
| 2006/0161081 A1 | 7/2006 | Barak et al. |
| 2006/0189907 A1 | 8/2006 | Pick et al. |
| 2006/0211965 A1 | 9/2006 | Horn et al. |

| | | |
|---|---|---|
| 2007/0038167 A1 | 2/2007 | Tabron et al. |
| 2007/0088239 A1 | 4/2007 | Roth et al. |
| 2007/0135742 A1 | 6/2007 | Meyer et al. |
| 2007/0135743 A1 | 6/2007 | Meyer |
| 2007/0135835 A1 | 6/2007 | McEwen et al. |
| 2007/0135836 A1 | 6/2007 | McEwen et al. |
| 2007/0161933 A1 | 7/2007 | Ravikumar |
| 2007/0167892 A1 | 7/2007 | Gramza et al. |
| 2007/0167895 A1 | 7/2007 | Gramza et al. |
| 2007/0179416 A1 | 8/2007 | Obrien et al. |
| 2007/0197943 A1 | 8/2007 | Hakonson et al. |
| 2007/0197944 A1 | 8/2007 | Bruce et al. |
| 2007/0197947 A1 | 8/2007 | Scott |
| 2007/0219580 A1 | 9/2007 | McEwen et al. |
| 2007/0244506 A1 | 10/2007 | McEwen et al. |
| 2007/0260162 A1 | 11/2007 | Meyer et al. |
| 2007/0276310 A1 | 11/2007 | Lipshaw et al. |
| 2007/0276311 A1 | 11/2007 | Wieringa et al. |
| 2007/0282233 A1 | 12/2007 | Meyer et al. |
| 2008/0000477 A1 | 1/2008 | Huster et al. |
| 2008/0004555 A1 | 1/2008 | Reis et al. |
| 2008/0004560 A1 | 1/2008 | Miskie |
| 2008/0021363 A1 | 1/2008 | Fee |
| 2008/0023423 A1 | 1/2008 | Duffy |
| 2008/0034479 A1 | 2/2008 | Barnett |
| 2008/0039756 A1 | 2/2008 | Thorsteinsson et al. |
| 2008/0039757 A1 | 2/2008 | Nordt, III et al. |
| 2008/0064996 A1 | 3/2008 | Bretl et al. |
| 2008/0071204 A1 | 3/2008 | Linnane et al. |
| 2008/0086071 A1 | 4/2008 | Weatherly |
| 2008/0103397 A1 | 5/2008 | Barak |
| 2008/0119771 A1 | 5/2008 | Jaccard |
| 2008/0188786 A1 | 8/2008 | Hickling |
| 2008/0208092 A1 | 8/2008 | Sawa |
| 2008/0234615 A1 | 9/2008 | Cook et al. |
| 2008/0243173 A1 | 10/2008 | Thorpe |
| 2008/0245361 A1 | 10/2008 | Brown |
| 2008/0249440 A1 | 10/2008 | Avitable et al. |
| 2008/0249442 A1 | 10/2008 | Brown et al. |
| 2008/0249443 A1 | 10/2008 | Avitable et al. |
| 2008/0249444 A1 | 10/2008 | Avitable et al. |
| 2008/0249447 A1 | 10/2008 | Brown et al. |
| 2008/0249449 A1 | 10/2008 | Brown et al. |
| 2008/0249455 A1 | 10/2008 | Brown et al. |
| 2008/0249559 A1 | 10/2008 | Brown et al. |
| 2008/0255485 A1 | 10/2008 | Johnson et al. |
| 2008/0281351 A1 | 11/2008 | Croushorn et al. |
| 2008/0312682 A1 | 12/2008 | Shams et al. |
| 2009/0005718 A1 | 1/2009 | Lightbourne |
| 2009/0064919 A1 | 3/2009 | Greenwald |
| 2009/0076432 A1 | 3/2009 | Winkler |
| 2009/0082708 A1 | 3/2009 | Scott et al. |
| 2009/0099562 A1 | 4/2009 | Ingimudarson et al. |
| 2009/0110890 A1 | 4/2009 | Garza et al. |
| 2009/0124944 A1 | 5/2009 | Ravikumar |
| 2009/0133446 A1 | 5/2009 | Burrow et al. |
| 2009/0163842 A1 | 6/2009 | Cropper |
| 2009/0171223 A1 | 7/2009 | McEwen et al. |
| 2009/0177222 A1 | 7/2009 | Brown et al. |
| 2009/0198261 A1 | 8/2009 | Schweikert |
| 2009/0227917 A1 | 9/2009 | Nardi |
| 2009/0227919 A1 | 9/2009 | Nardi et al. |
| 2009/0227922 A1 | 9/2009 | Nardi et al. |
| 2009/0234265 A1 | 9/2009 | Reid et al. |
| 2009/0278707 A1 | 11/2009 | Biggins et al. |
| 2009/0320174 A1 | 12/2009 | Turner |
| 2009/0326576 A1 | 12/2009 | Ben-Nun |
| 2010/0004575 A1 | 1/2010 | Vess |
| 2010/0042026 A1 | 2/2010 | Kloecker et al. |
| 2010/0042028 A1 | 2/2010 | Frank et al. |

FOREIGN PATENT DOCUMENTS

| | | |
|---|---|---|
| EP | 0303029 A1 | 2/1989 |
| EP | 0408049 A2 | 1/1991 |
| EP | 0552515 A1 | 7/1993 |
| EP | 0861651 A1 | 9/1998 |
| EP | 1018329 A2 | 7/2000 |
| EP | 1468816 A1 | 10/2004 |
| FR | 2813770 A1 | 3/2002 |
| GB | 2178663 A | 2/1987 |
| GB | 2183483 A | 6/1987 |
| GB | 2313784 A | 12/1997 |
| GB | 2373444 A | 9/2002 |
| JP | 59218154 A | 12/1984 |
| JP | 60135110 U | 9/1985 |
| JP | 2002065782 | 3/2002 |
| JP | 2004081709 | 3/2004 |
| JP | 2005066247 | 3/2005 |
| WO | WO 99/63892 | 12/1999 |
| WO | WO 2004/011842 A1 | 2/2004 |
| WO | 2005055913 A1 | 6/2005 |

OTHER PUBLICATIONS

Tyco Healthcare Kendall, SCD Soft Sleeve Catalog, Apr. 2001, pp. 1-2.
The Kendall Company, Vascular Therapy Products Catalog, Jan. 1996, pp. 8-5-8-7.
The Kendall Company, The New SCD Compression Sleeve, Aug. 1993, pp. 1-2.
Tyco Healthcare Kendall, Prevention Gets Personal, Mar. 2001, pp. 1, 2, 4.
Kendall SCD, Sequential Compression Sleeves, Patent Information, Jan. 1993, 6 pgs.
PCT International Search Report, May 25, 2005, 4 pgs.
PCT International Search Report, Jun. 2, 2005, 5 pgs.
PCT International Search Report, Jun. 2, 2005, 7 pgs.
PCT Invitation to Pay Additional Fees, Jun. 10, 2005, 6 pgs.
Mittelman, Jonathan S., MD: "Effectiveness of Leg Compression in Preventing Venous Stasis", The American Journal of Surgery, Dec. 1982, pp. 611-613, vol. 144, No. 6, Elsevier Publ., Bridgewater, NJ, USA.
Office action dated May 13, 2009 from U.S. Appl. No. 12/371,837, 11 pages.
Response filed Sep. 10, 2009 to Office action issued on May 13, 2009 from U.S. Appl. No. 12/371,837, 18 pages.
Office action dated Jul. 5, 2006 from U.S. Appl. No. 10/784,639, 8 pages.
Response filed Dec. 18, 2006 to Office action issued Jul. 5, 2006 in U.S. Appl. No. 10/784,639, 11 pages.
Final Office action dated Apr. 11, 2007 from U.S. Appl. No. 10/784,639, 10 pages.
Response filed Jun. 6, 2007 to Final Office action issued Apr. 11, 2007 U.S. Appl. No. 10/784,639, 9 pages.
Advisory Action dated Jun. 18, 2007 from U.S. Appl. No. 10/784,639, 3 pages.
Office action dated Sep. 4, 2007 from U.S. Appl. No. 10/784,639, 9 pages.
Response filed Jan. 17, 2008 to Office action issued Sep. 4, 2007 in U.S. Appl. No. 10/784,639, 11 pages.
Final Office action dated Mar. 14, 2008 from U.S. Appl. No. 10/784,639, 9 pages.
Response filed May 14, 2008 to final Office action issued Mar. 14, 2008 in U.S. Appl. No. 10/784,639, 11 pages.
Advisory action dated Jun. 13, 2008 from U.S. Appl. No. 10/784,639, 3 pages.
Amendment after notice of allowance dated Nov. 12, 2008 from U.S. Appl. No. 10/784,639, 15 pages.
Office Action entered in related U.S. Appl. No. 11/299,568 dated May 1, 2006, 7 pp.
Amendment after Non-Final Rejection submitted in related U.S. Appl. No. 11/299,568 dated Sep. 8, 2006, 12 pp.

Office Action entered in related U.S. Appl. No. 11/299,568 dated Dec. 1, 2006, 9 pp.

Amendment after Final Rejection submitted in related U.S. Appl. No. 11/299,568 dated Apr. 11, 2007, 4 pp.

Office Action entered in related U.S. Appl. No. 11/299,568 dated May 15, 2007, 3 pp.

Amendment after Non-Final Rejection submitted in related U.S. Appl. No. 11/299,568 dated May 23, 2007, 2 pp.

Office Action entered in related U.S. Appl. No. 11/299,568 dated Jun. 19, 2007, 4 pp.

Amendment after Non-Final Rejection submitted in related U.S. Appl. No. 11/299,568 dated Jun. 22, 2007, 1 p.

Office Action entered in related U.S. Appl. No. 11/299,568 dated Sep. 19, 2007, 6 pp.

Amendment after Non-Final Rejection submitted in related U.S. Appl. No. 11/299,568 dated Feb. 26, 2008, 7 pp.

Tyco Healthcare Kendall, SCD Response Brochure, Mar. 2000, pp. 1-2.

Tyco Healthcare Kendall, SCD Soft Sleeve Brochure, Apr. 2001, pp. 1-2.

* cited by examiner

COMPRESSION SLEEVE CONVERTIBLE IN LENGTH

BACKGROUND

1. Technical Field

The present disclosure generally relates to the field of vascular therapy for application to a limb of a body, and more particularly, to a compression apparatus having removable portions.

2. Description of the Related Art

A major concern for immobile patients and persons alike are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated to the heart. For example, when blood circulation in these veins is retarded due to illness, injury or inactivity, there is a tendency for blood to accumulate or pool. A static pool of blood is ideal for clot formations. A major risk associated with this condition is interference with cardiovascular circulation. Most seriously, a fragment of the blood clot can break loose and migrate. A pulmonary emboli can form blocking a main pulmonary artery, which may be life threatening.

The conditions and resulting risks associated with patient immobility may be controlled or alleviated by applying intermittent pressure to a patient's limb, such as, for example, a leg to assist in blood circulation. Known devices have been employed to assist in blood circulation, such as, one piece pads and compression boots. See, for example, U.S. Pat. Nos. 6,290,662 and 6,494,852.

For example, sequential compression devices have been used, which consist of an air pump connected to a disposable wraparound pad by a series of air tubes. The wraparound pad is placed around the patient's leg. Air is then forced into different parts of the wraparound pad in sequence, creating pressure around the calves and improving venous return.

These known devices may suffer from various drawbacks due to their bulk and cumbersome nature of use. These drawbacks reduce comfort, compliance and may disadvantageously prevent mobility of the patient as recovery progresses after surgery.

Therefore, it would be desirable to overcome the disadvantages and drawbacks of the prior art with a prophylaxis sequential compression apparatus that reduces bulk and is not cumbersome during use to improve comfort and compliance to a patient. It would be desirable if the prophylaxis sequential compression apparatus includes a removable portion to achieve the advantages of the present disclosure. It would be highly desirable if the prophylaxis sequential compression apparatus has a valve connector that facilitates quick disconnect from a pressurized fluid source. It is contemplated that the prophylaxis sequential compression apparatus is easily and efficiently manufactured.

SUMMARY

Accordingly, a compression apparatus is provided that reduces bulk and is not cumbersome during use to improve comfort and compliance to a patient for overcoming the disadvantages and drawbacks of the prior art. Desirably, the compression apparatus includes a removable portion to achieve the advantages of the present disclosure. Most desirably, the compression apparatus has a valve connector that facilitates quick disconnect from a pressurized fluid source. The compression apparatus is easily and efficiently fabricated.

The compression apparatus, in accordance with the principles of the present disclosure, includes a thigh length compression sleeve that converts to a knee length sleeve via tearing away or otherwise removing the thigh bladder and disconnecting the thigh bladder air supply line. In one embodiment, the thigh bladder air supply line will remove easily along with the thigh bladder, attaching at or near the point where the thigh bladder is removed from the sleeve. This would allow for a single motion to accomplish both removing of the thigh bladder and the thigh bladder supply line. The convertible sleeve allows the patient to use a more comfortable sleeve (knee vs. thigh) as risk for DVT decreases after surgery. This provides practitioners with various options while using a single apparatus.

In another embodiment, the compression apparatus is perforated for improved compliance and comfort with the patient during the overall length of time for wearing the apparatus. It is contemplated that the apparatus can be used with both nomadic and/or stationary compression systems. A pressurized fluid source continues to deliver pressurized fluid after removal of the valve. The pressurized fluid source can signal a high alarm if there are kinks in the tubing and a low alarm if there are leaks in the tubing. The compression apparatus is sequentially activated by increasing pressure through the tubes to correspond with the three portions of the sleeve. The distal end is the ankle bladder (high pressure), the proximal end is the thigh bladder (low pressure). The pressurized fluid source pumps air to the sleeve in a 60 second cycle with 11 seconds being compression and the rest being decompression.

In one embodiment, in accordance with the principles of the present disclosure, the compression apparatus includes a sleeve configured for disposal about a limb. The sleeve includes a first portion defining a first expandable chamber and a second portion defining a second expandable chamber and a third expandable chamber. The second portion includes a connector in fluid communication with a pressurized fluid source and the first expandable chamber, the second expandable chamber and the third expandable chamber thereby facilitating fluid communication between the pressurized fluid source and the chambers. The first portion is removable from the second portion.

The first portion is connected to the second portion via a perforated attachment. The first portion may be configured for disposal about a first part of the limb and the second portion is configured for disposal about a second part of the limb. The second expandable chamber may be disposed with the second portion for disposal about a second part of the limb and the third expandable chamber is disposed with the second portion for disposal about a third part of the limb.

Alternatively, the compression apparatus can include a variety of welds and bladders forming a quilting effect. For example, the first, second and third expandable chambers can each define at least one sub-chamber.

The sleeve may define at least one ventilation opening. The at least one opening can include openings formed in a surface of the expandable chambers. The at least one opening may include a slit disposed between the second expandable chamber and the third expandable chamber.

The connector can communicate with the chambers via a tubular pathway. The tubular pathway of the first expandable chamber may be removable from the connector. A pressurized fluid may be delivered to the chambers for expansion thereof in a sequential time interval such that, for example, the first expandable chamber is expanded, followed by (2.5 seconds later) the second expandable chamber, followed by (3 seconds later) the third expandable chamber to a total of 11 seconds from the start of the first expandable chamber. The chambers are then all simultaneously vented to the atmosphere.

In an alternate embodiment, the compression apparatus includes a sleeve configured to wrap about a leg and defining a plurality of ventilation openings. The sleeve includes a thigh portion defining a first inflatable chamber having sub-chambers. The sleeve further includes a calf portion defining a second inflatable chamber having sub-chambers and an ankle portion defining a third inflatable chamber having sub-chambers. The ankle portion includes a valve connector that fluidly communicates both a pressurized fluid source and the chambers via a tubular pathway to facilitate inflation of the chambers. The thigh portion is removably connected to the calf portion via a perforated attachment and the tubular pathway of the first inflatable chamber is removable from the valve connector.

In an alternate embodiment, the compression apparatus includes an expandable sleeve that is configured for disposal about a leg. The sleeve extends a length from below a knee of the leg to above the knee. The sleeve is convertible from the length extending from below the knee to above the knee, to a length extending solely below the knee. The length of the sleeve extending from below the knee to above the knee may include a first portion disposed about a thigh of the leg, the first portion being removable from the sleeve. The first portion may be connected to the sleeve via perforations.

In one method, the ankle bladder is compressed for 2½ seconds, the mid-section bladder is compressed for 2½ seconds and the proximal section bladder is also compressed for 2½ seconds. After the 11$^{th}$ second elapses, all bladders are vented simultaneously. The thigh portion may be torn away, thereby converting from a full leg to a knee length. A ventilation slit is disposed on the back of the calf portion. This dissipates heat, relieves itching and accommodates movement. A knit or hosiery under the compressive sleeve may be used.

In an alternate embodiment, a method of performing compression on a limb of a body includes the steps of providing a sleeve configured for disposal about the limb, the sleeve includes a first portion defining a first inflatable chamber and a second portion defining a second inflatable chamber and a third inflatable chamber, the second portion includes a connector in fluid communication with a pressurized fluid source and the chambers thereby facilitating fluid communication between the pressurized fluid source and the chambers, the first portion is removable from the second portion; disposing the sleeve about the limb; delivering pressurized fluid to the first inflatable chamber; delivering pressurized fluid to the second inflatable chamber; delivering pressurized fluid to the third inflatable chamber; deflating the chambers; and removing the first portion from the second portion.

The steps of delivering may each be performed for a duration of 2.5 seconds. The step of removing may include disconnecting the first inflatable chamber from the connector. The step of removing can include tearing the first portion from the second portion via a perforated attachment.

In an alternate embodiment, a method of performing compression on a limb of a body includes the steps of providing an expandable sleeve configured for disposal about a leg; disposing the sleeve about the limb such that the sleeve extends a length from below a knee of the leg to above the knee; delivering pressurized fluid to the sleeve; deflating the sleeve; and converting the sleeve from the length extending from below the knee to above the knee, to a length extending solely below the knee. The step of disposing the sleeve about the limb such that the sleeve extends a length from below a knee of the leg to above the knee can include a first portion of the sleeve being disposed about a thigh of the leg. The step of converting may include tearing the first portion from the sleeve.

BRIEF DESCRIPTION OF THE DRAWINGS

The objects and features of the present disclosure, which are believed to be novel, are set forth with the particularity in the appended claims. The present disclosure, both as to its organization and manner of operation, together with further objectives and advantages, may be best understood by reference to the following description, taken in connection with the accompanying drawings, which are described below.

DETAILED DESCRIPTION OF EXEMPLARY EMBODIMENTS

The exemplary embodiments of the compression apparatus and methods of operation disclosed are discussed in terms of vascular therapy including a prophylaxis compression apparatus for application to a limb of a body and more particularly in terms of a compression apparatus having removable portions. It is contemplated that the compression apparatus may be employed for preventing and overcoming the risks associated with patient immobility. It is further contemplated that the compression apparatus alleviates the conditions arising from patient immobility to prevent for example, DVT, peripheral edema, etc. It is contemplated that the compression apparatus according to the present disclosure may be attributable to all types of venous compression systems, including, but not limited to a prophylaxis sequential compression apparatus. The term "prophylaxis sequential" shall not be construed as limiting the general venous compression apparatus described herein. It is envisioned that the present disclosure, however, finds application with a wide variety of immobile conditions of persons and patients alike, such as, for example, those undergoing surgery, anesthesia, extended periods of bed rest, obesity, advanced age, malignancy, prior thromboembolism, etc.

In the discussion that follows, the term "proximal" refers to a portion of a structure that is closer to a torso of a subject and the term "distal" refers to a portion that is further from the torso. As used herein the term "subject" refers to a patient undergoing vascular therapy using the compression apparatus. According to the present disclosure, the term "practitioner" refers to an individual administering the compression apparatus and may include support personnel.

The following discussion includes a description of the compression apparatus, followed by a description of an exemplary method of operating the compression apparatus in accordance with the principals of the present disclosure. Reference will now be made in detail to the exemplary embodiments and disclosure, which are illustrated with the accompanying figures.

Figure 1:
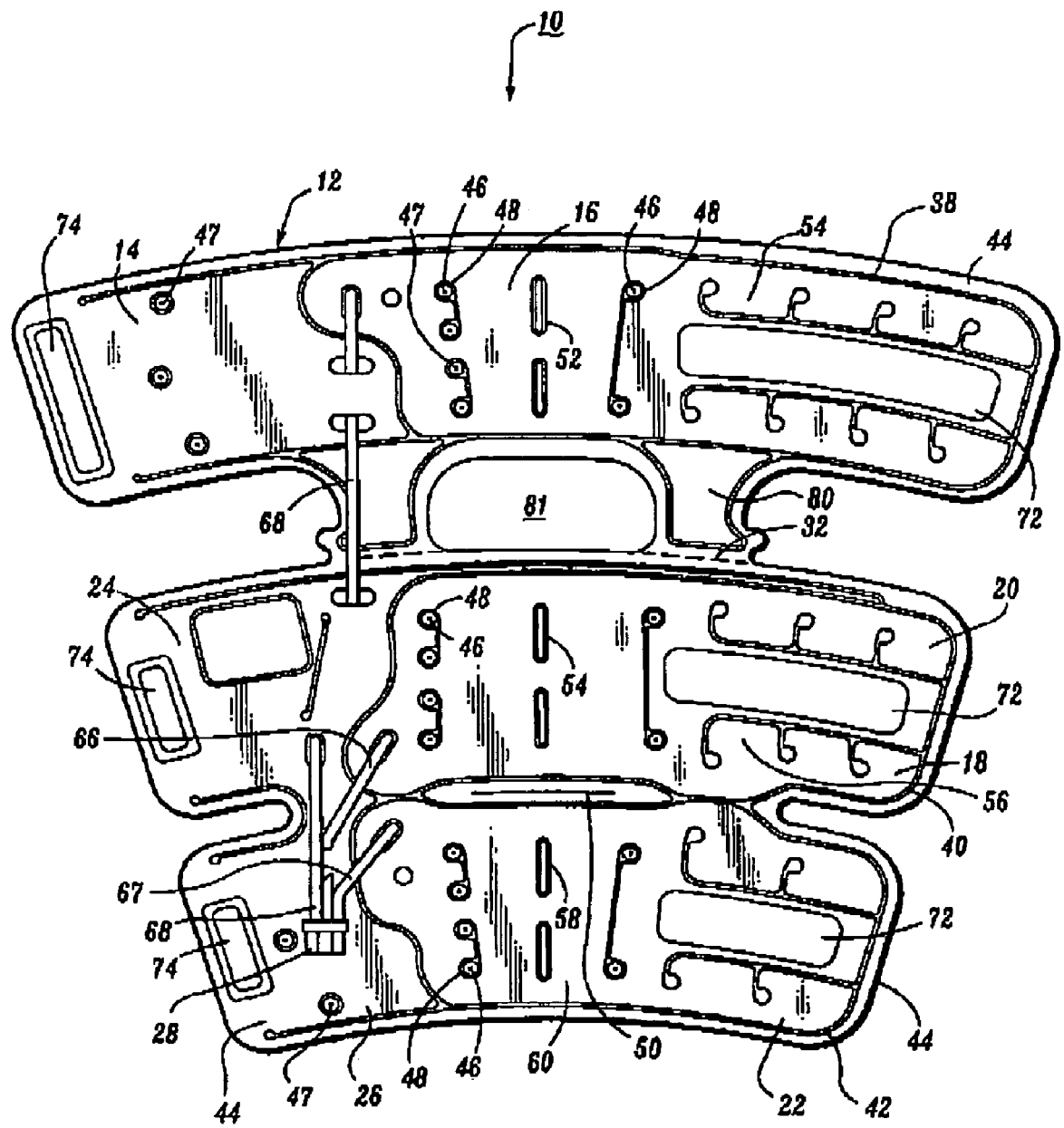
FIG. 1 is a perspective view of one particular embodiment of a compression apparatus in accordance with the principles of the present disclosure.
Figure 2:
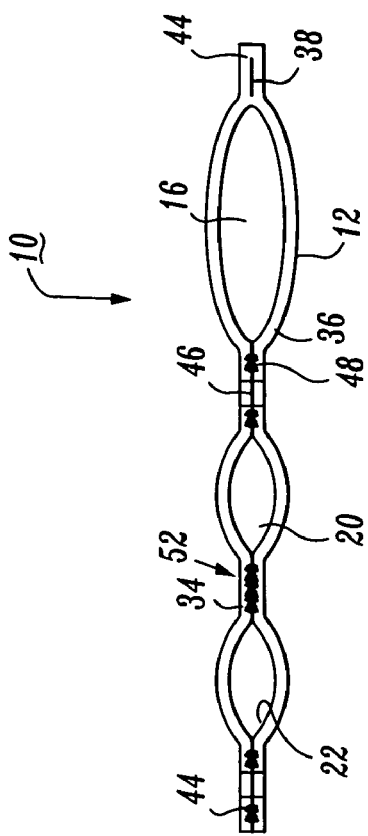
FIG. 2 is a side cross-sectional view of a chamber of the apparatus shown in FIG. 1.
Figure 5A:
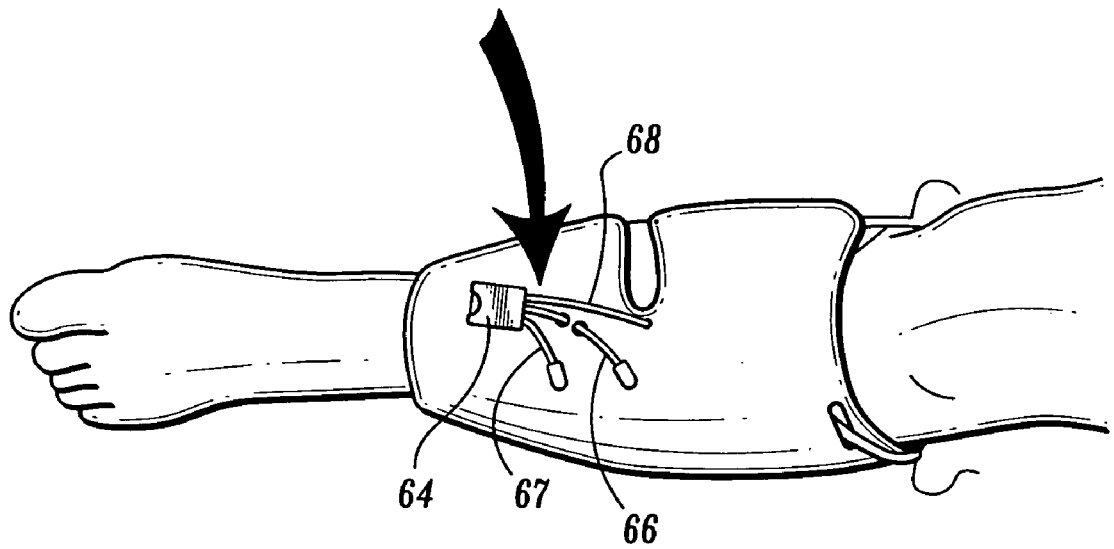
FIGS. 5A and 5B are perspective views of the apparatus shown in FIGS. 4A-4D whereby a tubular pathway of a portion of the apparatus is removed from the connector.

Turning now to the figures, wherein like components are designated by like reference numerals throughout the several views. Referring initially to FIGS. 1 and 2, there is illustrated a prophylaxis sequential compression apparatus 10, constructed in accordance with the principals of the present disclosure. Compression apparatus 10 includes a sleeve 12 configured for disposal about a limb, such as, for example, a leg L (FIGS. 4-6) of a subject's body. It is contemplated that sleeve 12 and other parts of compression apparatus 10 may be disposed, wrapped, mounted, etc., with various limbs, extremities, etc. of a subject's body, such as, for example, legs, arms, etc.

Sleeve 12 includes a first portion, such as, for example, thigh portion 14 that defines a first expandable chamber, such as, for example, first inflatable chamber 16. A second portion 18 of sleeve 12 defines a second expandable chamber, such as, for example, second inflatable chamber 20 and a third expandable chamber, such as, for example, third inflatable chamber 22. It is envisioned that the first portion 14 and the second portion 18 may include one or a plurality of expandable chambers. It is further envisioned that sleeve 12 or portions thereof may be disposable.

Second portion 18 has a calf portion 24 that includes second inflatable chamber 20 and an ankle portion 26 that includes third inflatable chamber 22. It is contemplated that the first portion and second portion 18 may be disposed about various portions of a subject's limb, according to the requirements of a particular vascular therapy application. Ankle portion 26 includes a valve connector 64 in fluid communication with a pressurized fluid source 30 via valve connector 28 and tubing 62 (FIGS. 4C and 4D) and chambers 16, 20 and 22 via a fluid pathway including tubing, as will be discussed below (see, for example, the valve connector described in U.S. patent application Ser. No. 10/784,639, filed on Feb. 23, 2004, publication No. US2005/0184264, and entitled Fluid Conduit Connector Apparatus, the entire contents of which is hereby incorporated by reference herein). Tubing 62 is made up of three separate tubes or lumens 65A, 65B and 65C. This configuration facilitates fluid communication between pressurized fluid 30 and chambers 16, 20 and 22.

Thigh portion 14 is removable from second portion 18. For example, calf portion 24 is removably connected to thigh portion 14 via a perforated attachment 32, as will be discussed. This removable configuration advantageously reduces the bulk of compression apparatus 10 via facile manipulation to increase comfort and compliance to a subject. Compression apparatus 10 also provides a subject with increased mobility. It is envisioned that sleeve 12 may include flexible sections, such as, elastic or spandex materials, disposed between the portions to facilitate mobility of a limb during use. For example, in FIG. 1, the thigh portion 14 is connected to the calf portion 24 by a flexible section 80 of reduced width having a knee opening 81 therein.

As best shown at FIGS. 1 and 2, sleeve 12 includes a top sheet 34 and a bottom sheet 36 that are overlaid to form the sleeve. Top sheet 34 and bottom sheet 36 are fixedly joined at seams that define inflatable chambers 16, 20 and 22. A seam 38 defines chamber 16, a seam 40 defines chamber 20 and a seam defines chamber 22. An edge 44 extends beyond seams 38, 40 and 42 about sleeve 12. It is contemplated that sleeve 12 includes a plurality of seams, disposed variously thereabout, that join top sheet 34 and bottom sheet 36. It is further contemplated that the seams may be welded, sewn, formed by adhesive, heat sealed, etc.

Top sheet 34 and bottom sheet 36 are fabricated from materials suitable for inflation of chambers 16, 20 and 22, such as, for example, films and fabrics, such as PVC (polyvinyl chloride) and PE (polyethylene), depending on the particular vascular therapy application and/or preference. Semi-flexible and flexible fabrics, such as urethanes and silicones may also be used. Sleeve 12 may include separate structure that include chambers 16, 20 and 22 and are disposed with or mounted to sheets 34, 36. One skilled in the art, however, will realize that other materials and fabrication methods suitable for assembly and manufacture, in accordance with the present disclosure, also would be appropriate.

Sleeve 12 defines vent openings, such as, for example sleeve apertures 46 that provide cooling to an adjacent portion of the limb of the subject. Sleeve apertures 46 pass completely through top sheet 34 and bottom sheet 36. This advantageously improves comfort to the subject during use. Sleeve 12 includes a weld portion 48 that surrounds sleeve aperture 46 to seal off the respective chamber from the aperture and prevent fluid communication therebetween. Sleeve 12 also includes vent holes 47 to provide cooling. It is envisioned that sleeve 12 may include a plurality of vent openings disposed variously thereabout.

A vent opening, such as, for example, vent slit 50 is disposed between inflatable chamber 20 and inflatable chamber 22. Vent slit 50 passes completely through top sheet 34 and bottom sheet 36. The vent slit advantageously provides cooling to the subject and increases mobility of the calf and ankle during use. It is contemplated that vent slit 50 may extend various lengths.

Thigh portion 14 includes an axial line of spot welds 52 that define sub-chambers 54 of inflatable chamber 16. Calf portion 24 similarly includes an axial line of spot welds 54 that define sub-chambers 56 of inflatable chamber 20 and ankle portion 26 includes spot welds 58 that define sub-chambers 60 of inflatable chamber 22. It is envisioned the sub-chambers may be alternatively formed via a continuous weld, adhesive, hot seal, etc. It is further envisioned that welds 58 may be disposed in various orientations to create alternative configurations for the sub-chambers.

Valve connector 28 communicates with chambers 16, 20 and 22 via a fluid pathway. The fluid pathway includes tubing 62 that connects valve connector 28 to pressurized fluid source 30, which may include a pump (see, for example, the controller pump described in U.S. patent application Ser. No. 10/784,323, filed on Feb. 23, 2004, now U.S. Pat. No. 7,354, 410, and entitled Compression Treatment System, the entire contents of which is hereby incorporated by reference herein). Pressurized fluid source 30 may be stationary or portable. It is contemplated that pressurized fluid source 30 may include the necessary electronics, computer software, etc. to carry out vascular therapy, in accordance with the principles of the present disclosure.

Figure 3:
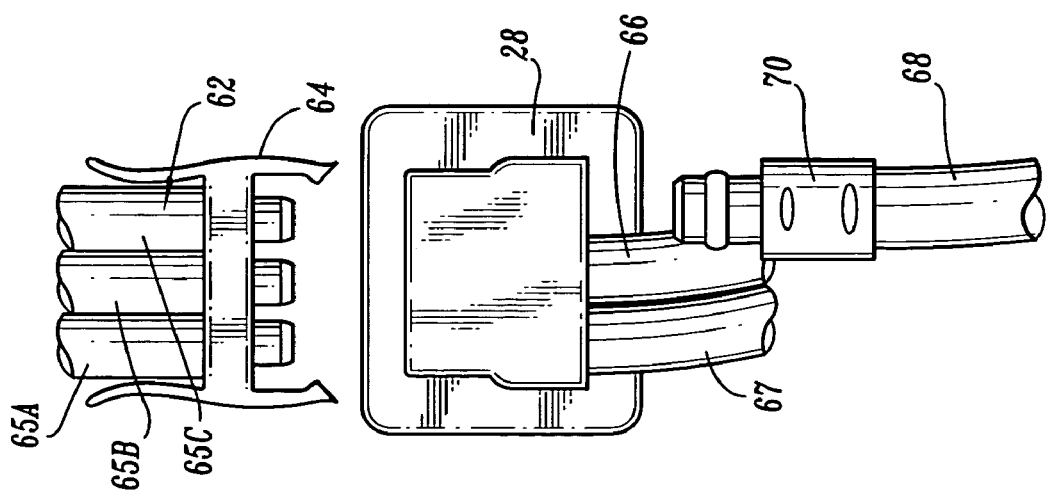
FIG. 3 is a top view of a connector of the apparatus shown in FIG. 1.
Figure 4A:
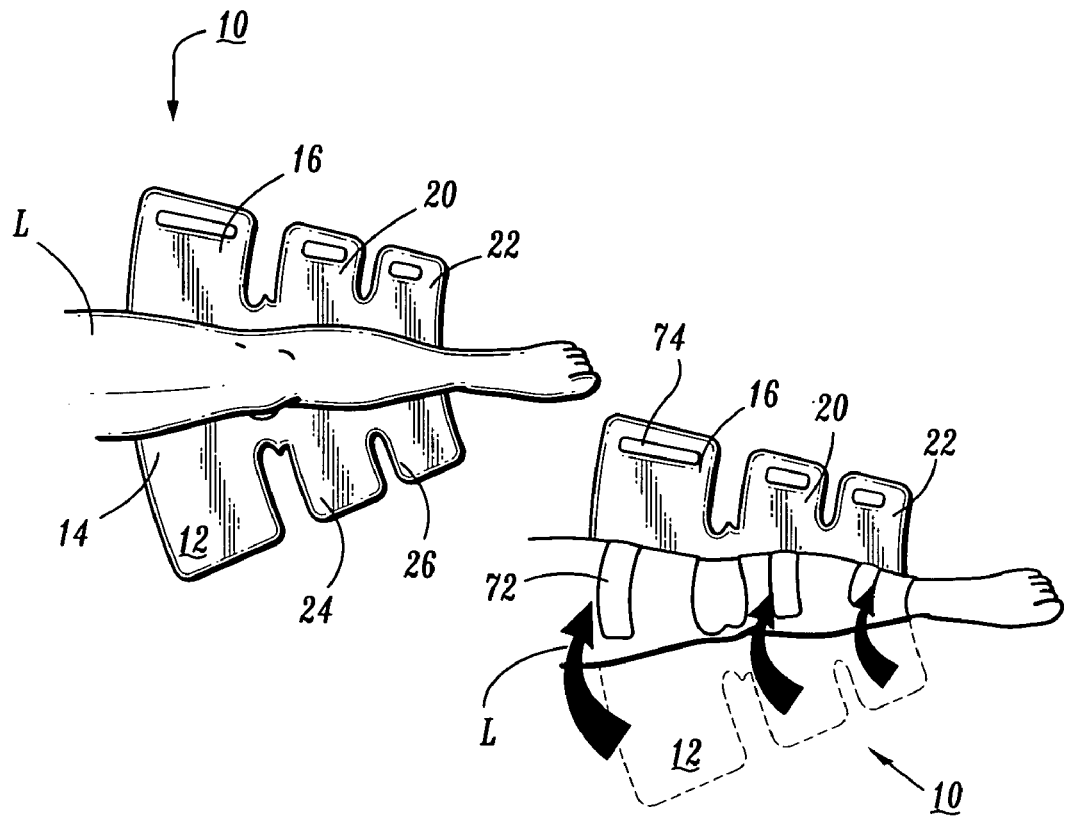
FIGS. 4A and 4B are perspective views of the apparatus shown in FIG. 1 disposed about a limb as well as a pressurized fluid source.
Figure 4B:
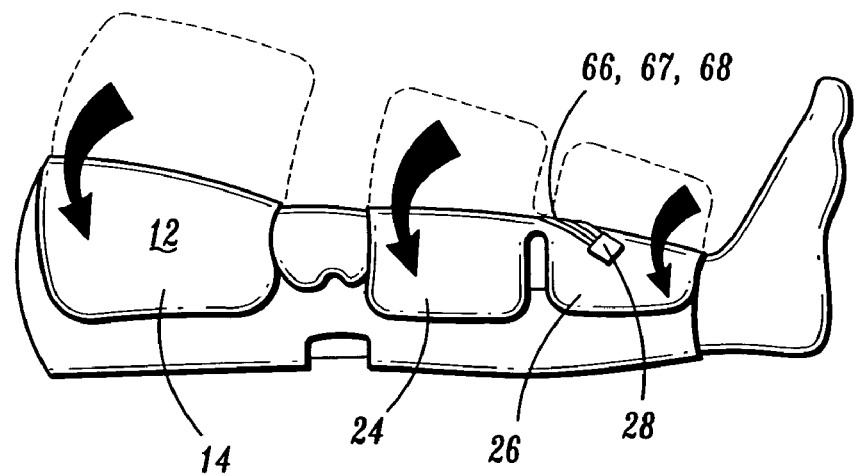
Figure 4C:
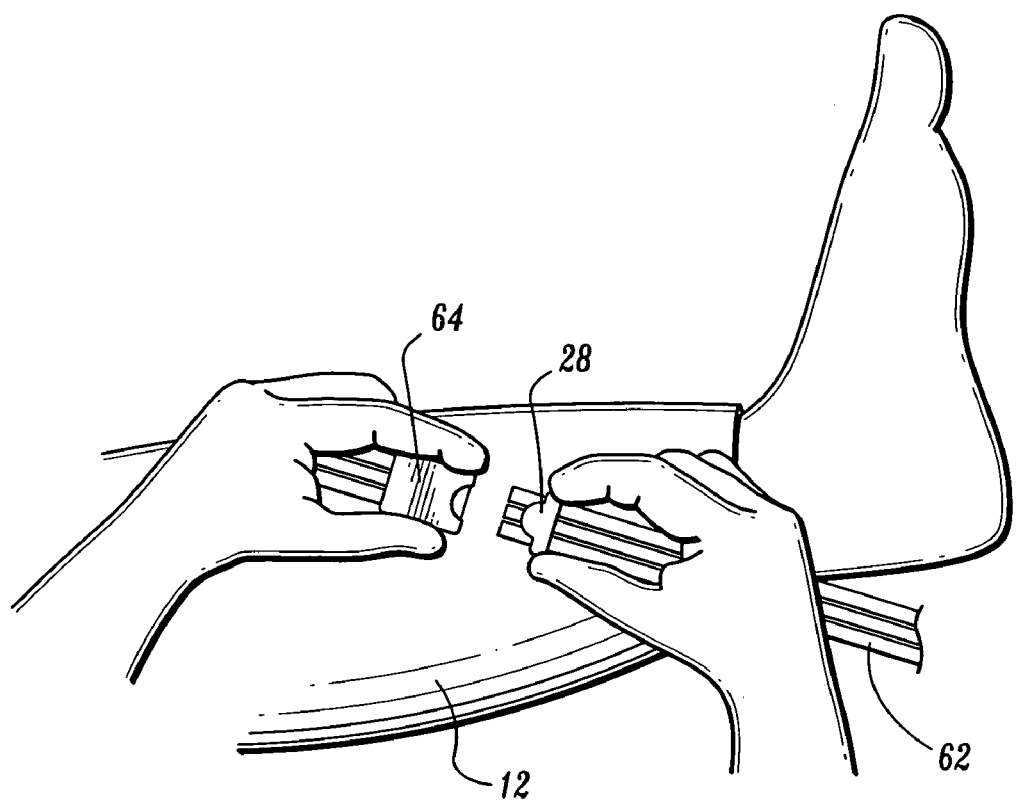
FIGS. 4C and 4D are perspective views of the apparatus shown.
Figure 4D:
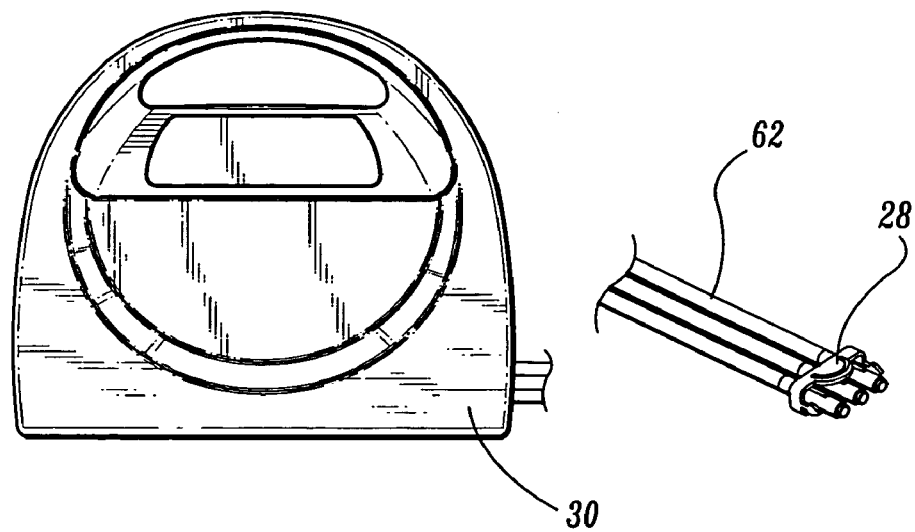

Tubing 62 attaches to valve connector 28 via a coupler 64, as shown in FIG. 3. Tubing 66 extends from valve connector 28 and fluidly connects to inflatable chamber 20. Tubing 67 extends from valve connector 28 and fluidly connects to inflatable chamber 22. Tubing 68 extends from valve connector 28 and fluidly connects to inflatable chamber 16. Tubing 68 includes a quick disconnect port 70. Port 70 attaches with valve connector 28 and is easily removable to facilitate removal of thigh portion 14 from calf portion 24. Tubing 62 and lumens 65A, 65B and 65C correspond with tubes 67, 66 and 68, respectively. It is envisioned that valve connector 28 may be fixed with sleeve 12, removable, tethered, etc. It is further envisioned that port 70 may be fixed with valve connector 28 and tubing 68 is removable from thigh portion 14.

Sleeve 12 includes securing parts, such as, for example, hook and loop pads 72 mounted in an orientation for engagement with corresponding hook and loop pads 74. Hook and loop pads 72, 74 enable secure mounting of sleeve 12 with leg L of a subject. It is contemplated that one or a plurality of securing parts that may be variously disposed about sleeve 12. It is further contemplated that the securing parts may include for example, clips, adhesive, pins, etc.

Referring to FIGS. 4-7, compression apparatus 10, similar to that described above, is assembled, sterilized and packaged for use. In operation, compression apparatus 10 is provided and manipulated for disposal about leg L of the subject. Tubing 66 is connected with calf portion 24 and tubing 67 is connected with ankle portion 26. Tubing 68 is connected to thigh portion 14. Tubing 66, 67 and 68 is connected to valve connector 28, which is connected with tubing 62 and pressurized fluid source 30 (FIGS. 4C and 4D). Therefore, the fluid pathway of compression apparatus 10 establishes fluid communication between pressurized fluid source 30 and chambers 16, 20 and 22.

Figure 7:
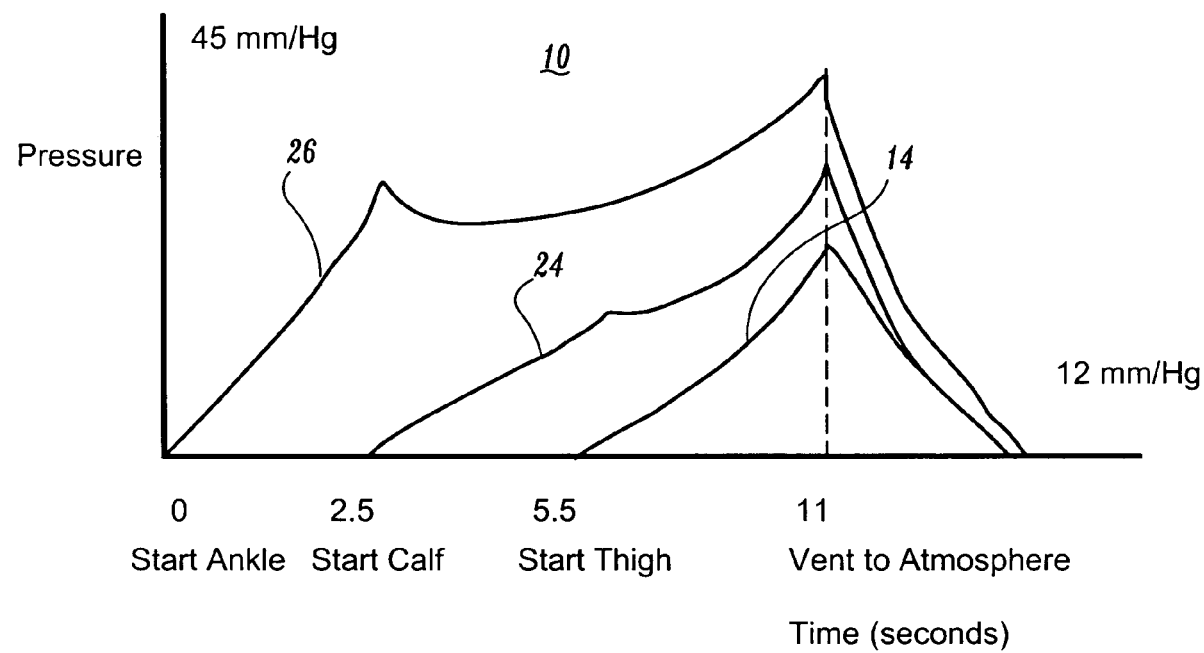
FIG. 7 is a pressure versus time plot illustrating sequential compression of the apparatus shown in FIG. 1.

Sleeve 12 is wrapped about leg L and secured thereto via hook and loop pads 72, 74, discussed above, as shown in FIGS. 4A and 4B. Sleeve 12 extends a length from below a knee of leg L, via second portion 18, to above the knee, via thigh portion 14. Compression apparatus 10 is sequentially activated by delivering pressurized fluid to chambers 16, 20 and 22 via the fluid pathway. In one embodiment and as shown at FIG. 7, pressurized fluid source 30 delivers air to sleeve 12 in a 60 second cycle including 11 seconds in compression and 49 seconds in decompression. Compressed air is delivered to inflatable chamber 22 for 2.5 seconds. Then, compressed air is delivered to inflatable chamber 20 for 2.5 seconds. Compressed air is then delivered to inflatable chamber 16 for 2.5 seconds. Compression apparatus 10 maintains inflation for several seconds until the 11$^{th}$ second and then chambers 16, 20 and 22 are deflated simultaneously. It is contemplated that this sequential compression may continue for a plurality of cycles, according to the requirements of a particular vascular therapy application. Other sequential compression cycles are also contemplated. It is envisioned that various forms of fluid may be delivered to sleeve 12, such as, for example, liquid, gases, etc.

Figure 5B:
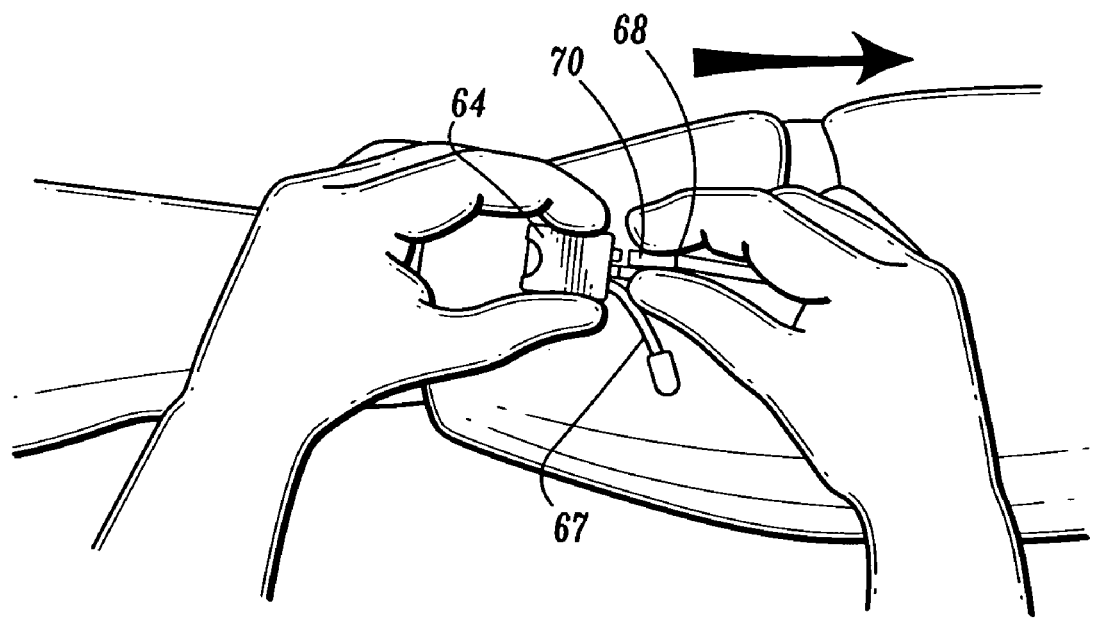
Figure 6A:
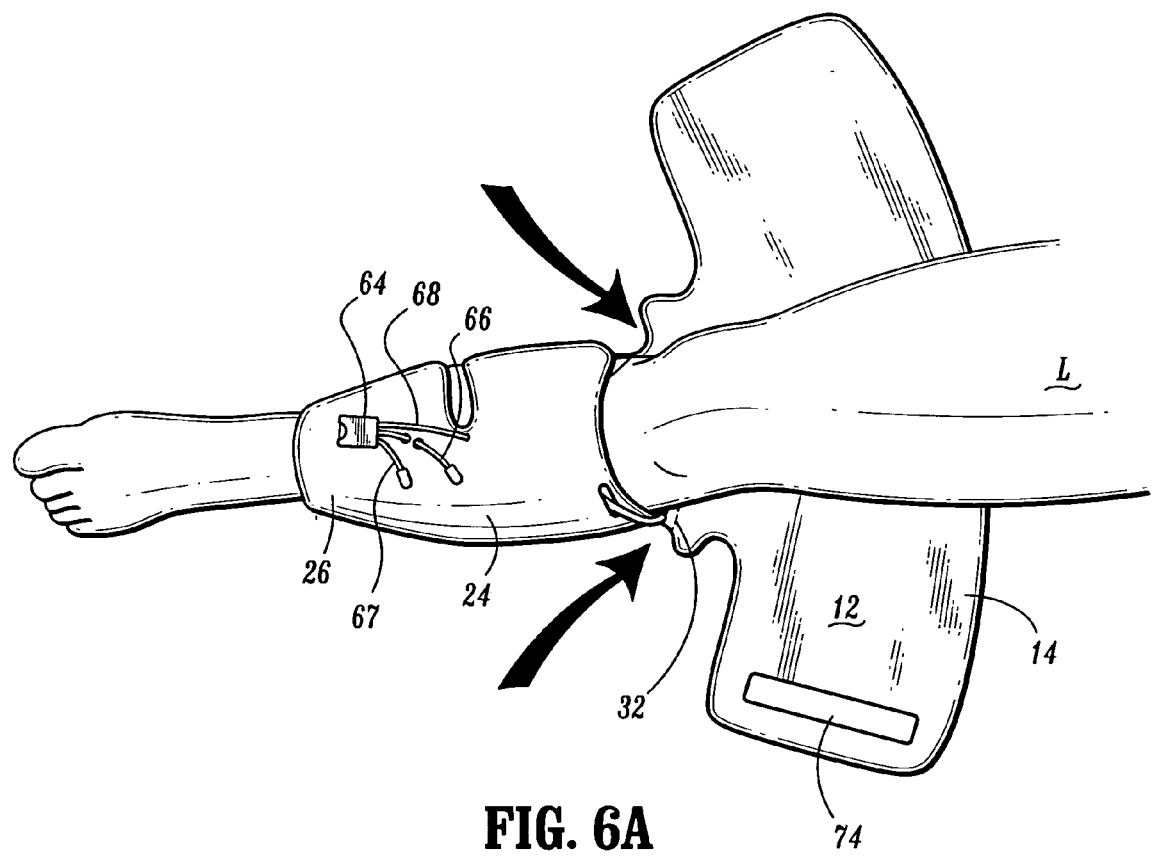
FIGS. 6A and 6B are perspective views of the apparatus shown in FIG. 5 whereby a portion of the apparatus is removed.
Figure 6B:
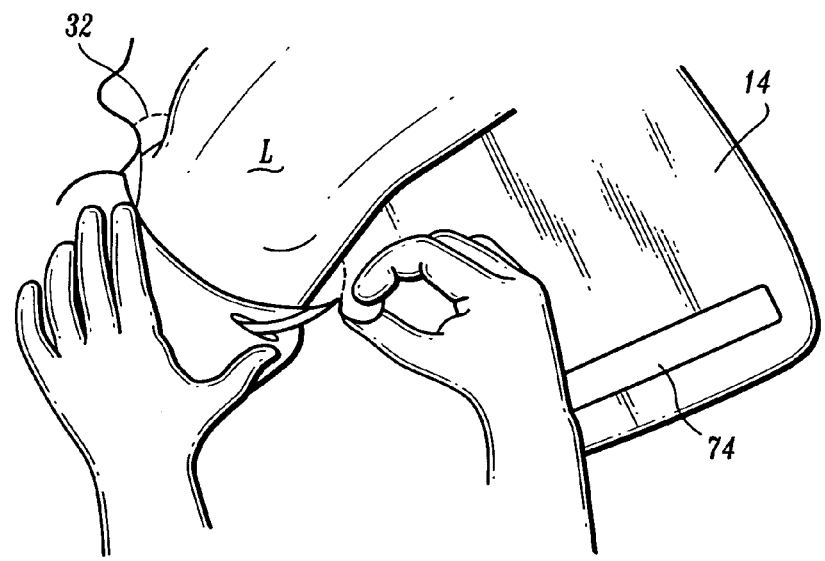

After desired period of time for sequential compression elapses, e.g., recovery time, etc. pursuant to the requirements of a particular vascular therapy application, thigh portion 14 may be removed from second portion 18. Thus, sleeve 12 is convertible from the length extending from below the knee to above the knee, to a length extending solely below the knee. Sleeve 12 is manipulated such that thigh portion 14 is removed and torn completely from calf portion 24 via perforations 32 extending continuously across the flexible section 80 of the sleeve from adjacent one boundary edge of the sleeve to adjacent an opposite boundary edge of the sleeve at a location below the knee opening 81 in the sleeve, the first and second portions of the sleeve being located on opposite sides of the perforations, as shown in FIGS. 6A and 6B. Port 70, connected to tubing 68, is easily manipulated to quick disconnect from valve connector 28, as shown in FIG. 5B. The remaining portion of sleeve 12, second portion 18 including calf portion 24 and ankle portion 26, is stand alone and continues to operate as described above. This converts sleeve 12 from a full leg length apparatus to a knee length apparatus. Compression apparatus 10 may be employed to completion of a desired vascular therapy application. Other methods of use are also contemplated, for example, the thigh portion 14 may not be removed and remain with the sleeve 12.

As stated above, upon the optional removal of thigh portion 14, a user or practitioner disconnects tubing member 68 and disconnect port 70 from connector 28. Connector 28 (and optionally disconnect port 70) is configured such that upon separation of tube 68 from connector 28, a desired amount of fluid flow from fluid source 30 is continuously achieved through the connector 28. Such continued fluid flow is desirable to maintain continuity with the pressurized fluid source 30. That is, fluid flow adjustments to the fluid source 30 need not be made if a user or practitioner decides to remove thigh portion 14 from the compression apparatus 10. Even after removal of thigh portion 14, the pressurized fluid source 30 will continue to deliver the same amount of fluid and pressure through tubing 65C into connector 28 and out into the atmosphere.

Figure 8:
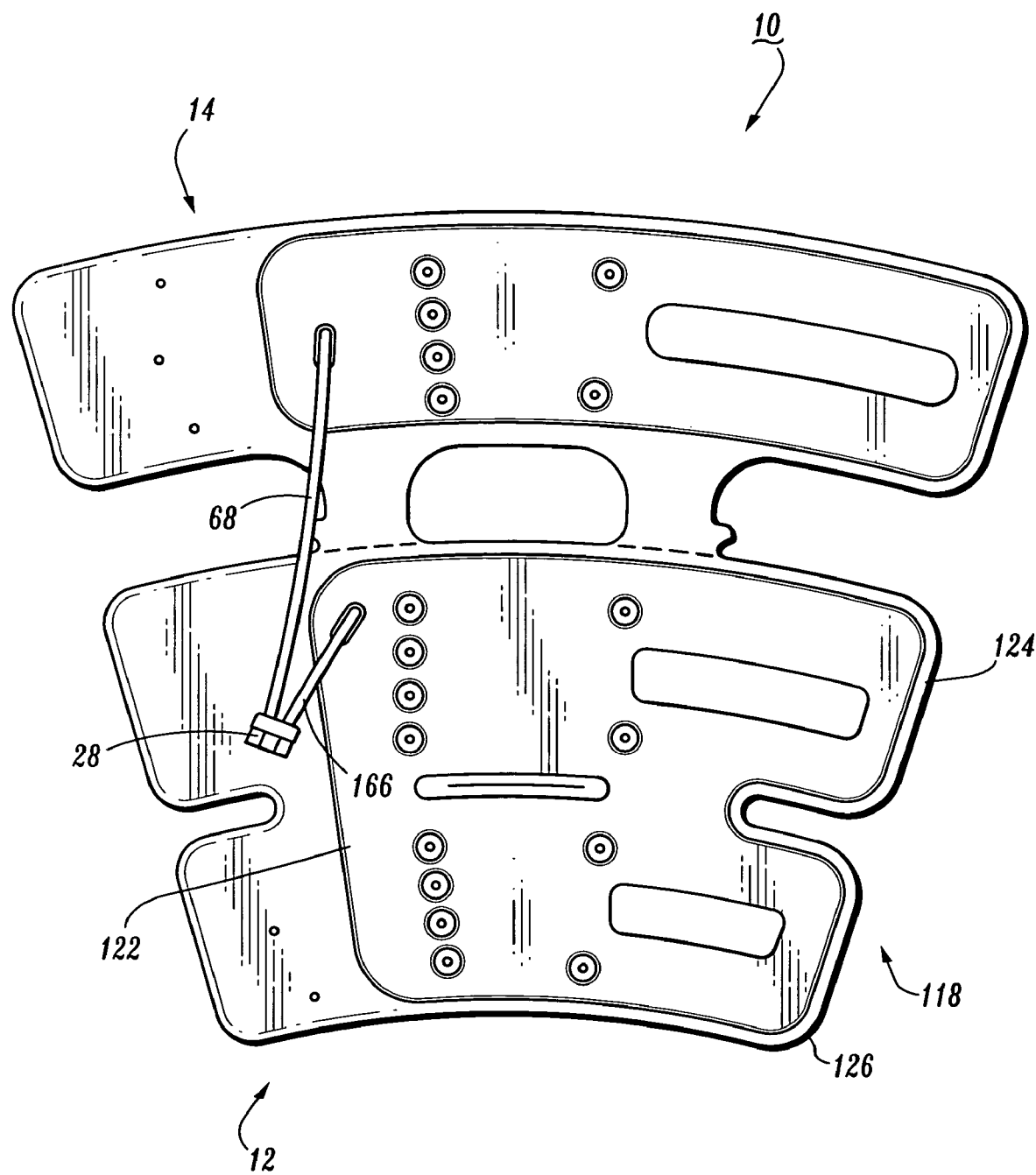
FIG. 8 is an alternate embodiment of the compression apparatus shown in FIG. 1.

Referring to FIG. 8, an alternate embodiment of compression apparatus 10 is shown. Sleeve 12, similar to that described above, includes thigh portion 14 and a second portion 118. Second portion 118 has a calf portion 124 and an ankle portion 126 that include an inflatable chamber 122. Pressurized fluid source 30 (FIG. 1) fluidly communicates with sleeve 12 via valve connector 28 and tubing 62 (FIG. 1). Valve connector 28 fluidly communicates with chambers 16 and 122 via separate tubes 68 and 166, respectively, for employment similar to that described above, including the optional removal of thigh portion 14 via perforations 32.

It will be understood that various modifications may be made to the embodiments disclosed herein. For example, the tear away and removable features of the instant compression apparatus 10 may be employed with other compression apparatuses (see, compression apparatus described in U.S. patent application Ser. No. 10/784,640, filed on Feb. 23, 2004, now U.S. Pat. No. 6,994,125, and entitled Compression Apparatus, the entire contents of which is hereby incorporated by reference herein). Therefore, the above description should not be construed as limiting, but merely as exemplification of the various embodiments. Those skilled in the art will envision other modifications within the scope and spirit of the claims appended hereto.

What is claimed is:

1. A method of performing sequential compression on a limb of a body comprising the steps of:

providing a sleeve configured for disposal about the limb, the sleeve including a first portion defining a first inflatable chamber and a second portion defining a second inflatable chamber and a third inflatable chamber, the first, second and third inflatable chambers being arranged with respect to each other lengthwise along the sleeve, the second portion including a connector in fluid communication with a pressurized fluid source and the first, second, and third chambers via a first tubing, a second tubing, and a third tubing extending from the connector to respective chambers, thereby facilitating fluid communication between the pressurized fluid source and the chambers, the first portion of the sleeve being removable from the second portion of the sleeve, and the first tubing being removable from the connector;

disposing the sleeve about the limb;
delivering pressurized fluid to the first inflatable chamber, the second inflatable chamber and the third inflatable chamber to inflate the chambers in a sequence for moving blood lengthwise of the limb;
completely removing the first portion of the sleeve from the second portion of the sleeve by tearing the sleeve along perforations in the sleeve at a location where the first tubing crosses the perforations;
removing the first tubing from the connector while leaving the second and third tubing connected to the connector; and
delivering a pressurized fluid to inflate the second and third inflatable chambers in a sequence for moving blood lengthwise of the limb after the first portion of the sleeve is removed from the second portion of the sleeve and after the first tubing is removed from the connector.

2. A method of performing compression as recited in claim 1, wherein the steps of delivering are each performed for a duration of between 2.5 and 5.5 seconds.

3. A method of performing sequential compression on a limb of a body comprising the steps of:
providing an expandable sleeve configured for disposal about a leg;
disposing the sleeve about the limb such that the sleeve extends a length from below a knee of the leg to above the knee;
sequentially delivering, via a tubular pathway, pressurized fluid from a source of pressurized fluid to inflatable ankle, calf and thigh portions of the sleeve to move blood lengthwise of the limb of the patient, said tubular pathway comprising first tubing extending from a connector to the inflatable thigh portion of the sleeve, second tubing extending from the connector to the inflatable calf portion of the sleeve, and third tubing extending from the connector to the inflatable ankle portion of the sleeve;
deflating the ankle, calf and thigh portions of the sleeve; and
converting the sleeve from the length extending from below the knee to above the knee, to a length extending solely below the knee by tearing the sleeve along perforations in the sleeve at a location where the first tubing crosses the perforations to completely remove the thigh portion of the sleeve extending above the knee, and by removing the first tubing from the connector while leaving the second and third tubing connected to the connector, the perforations being configured such that the calf and ankle portions of the sleeve remain intact after the thigh portion is torn away to permit sequential inflation of the calf and ankle portions after said thigh portion of the sleeve is removed and after said first tubing is removed from the connector.

4. A method of performing compression as recited in claim 3, wherein the thigh and calf portions of the sleeve are connected by a flexible section of reduced width having a knee opening therein, and wherein said perforations extend across the flexible section at a location below the knee opening.

5. A compression apparatus for carrying out sequential compression vascular therapy on a limb of a patient, comprising:
a sleeve configured for disposal about a limb and having boundary edges,
the sleeve including a first portion defining a first expandable chamber and a second portion defining a second expandable chamber and a third expandable chamber, the first, second and third expandable chambers being arranged with respect to each other lengthwise along the sleeve to move blood lengthwise of the limb,
the second portion including a connector for fluidly connecting a pressurized fluid source to the first expandable chamber, the second expandable chamber and the third expandable chamber whereby fluid can be delivered from said pressurized fluid source to said chambers to carry out said vascular therapy,
the first portion of the sleeve being completely removable from the second portion of the sleeve,
perforations in the sleeve extending continuously across the sleeve from adjacent one boundary edge of the sleeve to adjacent an opposite boundary edge of the sleeve, said first and second portions of the sleeve being located on opposite sides of the perforation whereby the sleeve may be torn along the perforations to completely remove the first portion of the sleeve from the second portion of the sleeve while leaving the second portion of the sleeve intact for delivery of fluid from said pressurized source to said second and third expandable chambers arranged with respect to each other lengthwise along the sleeve to permit sequential compression vascular therapy on said limb after said first portion of the sleeve is removed,
wherein the connector communicates with the chambers via a tubular pathway comprising first tubing extending from the connector and fluidly connecting to the first expandable chamber, second tubing extending from the connector and fluidly connecting to the second expandable chamber, and third tubing extending from the connector and fluidly connecting to the third expandable chamber, and
wherein said first tubing extends from the connector across the perforations to the first expandable chamber.

6. A compression apparatus as recited in claim 5, wherein the first portion is configured for disposal about a first part of the limb and the second portion is configured for disposal about a second part of the limb.

7. A compression apparatus as recited in claim 5, wherein the second expandable chamber is disposed with the second portion for disposal about a second part of the limb and the third expandable chamber is disposed with the second portion for disposal about a third part of the limb.

8. A compression apparatus as recited in claim 5, wherein the first expandable chamber defines at least one sub-chamber.

9. A compression apparatus as recited in claim 8, wherein the second expandable chamber defines at least one sub-chamber.

10. A compression apparatus as recited in claim 9, wherein the third expandable chamber defines at least one sub-chamber.

11. A compression apparatus as recited in claim 5, wherein the sleeve defines at least one ventilation opening.

12. A compression apparatus as recited in claim 11, wherein the at least one opening includes openings formed in a surface of the expandable chambers.

13. A compression apparatus as recited in claim 11, wherein the at least one opening includes a slit disposed between the second expandable chamber and the third expandable chamber.

14. A compression apparatus as recited in claim 5, further comprising a quick disconnect port permitting easy removal of the first tubing from the connector when the first portion of the sleeve is removed from the second portion of the sleeve, said second tubing and said third tubing remaining attached to the connector when the first portion of the sleeve is removed from the second portion of the sleeve.

15. A compression apparatus as recited in claim 14, wherein said connector comprises a valve for partially closing said quick disconnect port when the first tubing is removed from said connector such that fluid from said pressurized fluid source continues to flow from the port and said sequential compression vascular therapy is able to continue without interruption.

16. A compression apparatus as recited in claim 15, wherein the first and second portions of the sleeve are connected by a flexible section of reduced width having a knee opening therein, and wherein said perforations extend across the flexible section at a location below the knee opening.

17. A compression apparatus for carrying out sequential compression vascular therapy on a patient, comprising:
   a sleeve configured to wrap about a leg and having boundary edges,
   the sleeve including a thigh portion defining a first inflatable chamber having sub-chambers, the sleeve further including a calf portion defining a second inflatable chamber having sub-chambers and an ankle portion defining a third inflatable chamber having sub-chambers, the first, second and third inflatable chambers being arranged with respect to each other lengthwise along the sleeve to move blood lengthwise of the limb
   the ankle portion of the sleeve including a valve connector for fluidly connecting a pressurized fluid source to the chambers via a tubular pathway, the pressurized fluid is delivered from said pressurized fluid source to said chambers to carry out said vascular therapy,
   said tubular pathway comprising first tubing extending from the valve connector and fluidly connecting to the first inflatable chamber, second tubing extending from the valve connector and fluidly connecting to the second inflatable chamber, and third tubing extending from the valve connector and fluidly connecting to the third inflatable chamber,
   the thigh portion of the sleeve being removably connected to the calf portion of the sleeve via perforations in the sleeve extending continuously across the sleeve from adjacent one boundary edge of the sleeve to adjacent an opposite boundary edge of the sleeve, said thigh and calf portions of the sleeve being located on opposite sides of the perforations whereby the sleeve may be torn along the perforations to completely remove the thigh portion from the calf portion while leaving the calf and ankle portions of the sleeve intact for delivery of fluid from said pressurized source to said second and third inflatable chambers arranged with respect to each other lengthwise along the sleeve to permit sequential compression vascular therapy on said limb after said thigh portion of the sleeve is removed,
   wherein said first tubing extends from the valve connector across the perforations to the first inflatable chamber, and
   wherein the first tubing of the tubular pathway is removable from the valve connector when the thigh portion is removed from the calf portion, and the second tubing and third tubing remaining attached to the valve connector when the thigh portion is removed from the calf portion to permit sequential inflation of said second and third inflatable chambers after said thigh portion of the sleeve is removed.

18. A compression apparatus as recited in claim 17, wherein the sleeve further includes a ventilation slit disposed between the second inflatable chamber and the third inflatable chamber.

19. A compression apparatus as recited in claim 17, wherein the thigh and calf portions of the sleeve are connected by a flexible section of reduced width having a knee opening therein, and wherein said perforations extend across the flexible section at a location below the knee opening.

20. A compression device as set forth in claim 19 wherein said first tubing extends from the connector over the perforations at one side of the knee opening.

21. A compression device as set forth in claim 19 wherein said first tubing is connected to the thigh and calf portions of the sleeve but is not connected to the ankle portion of the sleeve.

22. A compression apparatus for carrying out sequential compression vascular therapy on a patient, comprising:
   an expandable sleeve configured for disposal about a leg, said sleeve having boundary edges, the sleeve extending a length from below a knee of the leg to above the knee, wherein the sleeve is convertible from the length extending from below the knee to above the knee, to a length extending solely below the knee by tearing an inflatable thigh portion of the sleeve completely away from inflatable calf and ankle portions of the sleeve along perforations in the sleeve extending continuously across the sleeve from adjacent one boundary edge of the sleeve to adjacent an opposite boundary edge of the sleeve, the perforations being configured such that the calf and ankle portions of the sleeve remains intact after the thigh portion is torn away to permit sequential inflation of the calf and ankle portions whereby sequential compression vascular therapy on said patient can be carried out after said thigh portion of the sleeve is removed, and
   a connector on the calf or ankle portion of the sleeve communicating with the thigh, calf and ankle portions of the sleeve via a tubular pathway comprising first tubing extending from the connector and fluidly connecting to the inflatable thigh portion of the sleeve, second tubing extending from the connector and fluidly connecting to the inflatable calf portion of the sleeve, and third tubing extending from the connector and fluidly connecting to the inflatable ankle portion of the sleeve, and
   wherein said first tubing extends from the connector across the perforations to the inflatable thigh portion of the sleeve.

23. A compression apparatus as recited in claim 22, wherein the thigh and calf portions of the sleeve are connected by a flexible section of reduced width having a knee opening therein, and wherein said perforations extend across the flexible section at a location below the knee opening.

24. A compression apparatus adapted for inflation and deflation by a pressurized fluid source for carrying out sequential compression vascular therapy on a patient, comprising:
   a sleeve configured for disposal about a limb and having boundary edges,
   the sleeve including a first portion defining a first expandable chamber and a second portion defining a second expandable chamber and a third expandable chamber, the first, second and third expandable chambers being arranged with respect to each other lengthwise along the sleeve to move blood lengthwise of the limb,
   the second portion including a connector for fluidly connecting said pressurized fluid source to the first expandable chamber, the second expandable chamber and the third expandable chamber, the fluid being delivered from said pressurized fluid source to said chambers to carry out said vascular therapy, perforations in the sleeve extending continuously across the sleeve from adjacent one boundary edge of the sleeve to adjacent an opposite boundary edge of the sleeve, said first and second portions of the sleeve being located on opposite sides of the perforations, the sleeve is torn along the perforations to completely remove the first portion of the sleeve from the second portion of the sleeve while leaving the second portion of the sleeve intact for delivery of fluid from said pressurized source to said second and third expandable chambers arranged with respect to each other lengthwise along the sleeve to permit sequential compression vascular therapy on said limb after said first portion of the sleeve is removed, first tubing extending from the connector across the perforations and fluidly connecting to the first expandable chamber, second tubing extending from the connector and fluidly connecting to the second expandable chamber, third tubing extending from the connector and fluidly connecting to the third expandable chamber, said first tubing comprising a quick disconnect port communicating with a fluid port in said connector permitting easy removal of the first tubing from a downstream side of the connector when the first portion of the sleeve is completely removed from the second portion of the sleeve, said second tubing and said third tubing remaining attached to the connector when the first portion of the sleeve is removed from the second portion of the sleeve, and said connector comprising a valve for partially closing said fluid port when the first tubing is removed from said connector, the fluid continues to flow from the fluid port and said inflation and deflation by said pressurized fluid source is able to continue without interruption.

25. A compression apparatus as recited in claim 24 wherein said valve is movable when the first tubing is removed from the connector to reduce fluid flow from the pressurized fluid source through said fluid port to a level approximating flow to said first expandable chamber prior to removal of the first portion of the sleeve from the second portion of the sleeve.

26. A compression device as set forth in claim 24, wherein the first and second portions of the sleeve are connected by a flexible section of reduced width having a knee opening therein, and wherein said perforations extend across the flexible section at a location below the knee opening.

* * * * *